United States Patent
Lowry et al.

(10) Patent No.: US 11,213,513 B2
(45) Date of Patent: Jan. 4, 2022

(54) COMPOSITIONS AND METHODS FOR PROMOTING HAIR GROWTH WITH MPC1 INHIBITORS

(71) Applicant: The Regents of the University of California, Oakland, CA (US)

(72) Inventors: William E. Lowry, Los Angeles, CA (US); Heather R. Christofk, Los Angeles, CA (US); Aimee Flores, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 16/488,451

(22) PCT Filed: Aug. 25, 2017

(86) PCT No.: PCT/US2017/048701
§ 371 (c)(1),
(2) Date: Aug. 23, 2019

(87) PCT Pub. No.: WO2018/039612
PCT Pub. Date: Mar. 1, 2018

(65) Prior Publication Data
US 2020/0030289 A1    Jan. 30, 2020

Related U.S. Application Data

(60) Provisional application No. 62/463,232, filed on Feb. 24, 2017.

(51) Int. Cl.
*A61K 31/405* (2006.01)
*A61K 8/49* (2006.01)
(Continued)

(52) U.S. Cl.
CPC ............ *A61K 31/405* (2013.01); *A61K 8/492* (2013.01); *A61K 9/0014* (2013.01); *A61K 9/107* (2013.01); *A61P 17/14* (2018.01); *A61Q 7/00* (2013.01)

(58) Field of Classification Search
None
See application file for complete search history.

(56) References Cited

U.S. PATENT DOCUMENTS 6,541,507 B1 * 4/2003 Dalko .................... A61K 8/492
514/429
2010/0305187 A1  12/2010 Guelow et al.
(Continued)

FOREIGN PATENT DOCUMENTS

CN    106880693 A    6/2017
EP    1068858 A1    1/2001
(Continued)

OTHER PUBLICATIONS

Wang et al., "Oxidative stress and substance P mediate psychological stress-induced autophagy and delay of hair growth in mice", Arch. Dermatol. Res., 307:171-181 (Year: 2015).*
(Continued)

*Primary Examiner* — Melissa L Fisher
*Assistant Examiner* — Barbara S Frazier
(74) *Attorney, Agent, or Firm* — Foley Hoag LLP; David P. Halstead; Alexander J. Chatterley

(57) ABSTRACT

Provided herein are methods of accelerating, promoting, or restoring hair growth, comprising administering to a subject in need thereof an effective amount of a compound of formula (I). Also provided are compositions comprising the compound of formula (I).

20 Claims, 43 Drawing Sheets

(51) Int. Cl.
*A61K 9/00* (2006.01)
*A61K 9/107* (2006.01)
*A61P 17/14* (2006.01)
*A61Q 7/00* (2006.01)

(56) References Cited

U.S. PATENT DOCUMENTS

| | | |
|---|---|---|
| 2015/0140071 A1 | 5/2015 | Rajasekaran |
| 2020/0030289 A1 | 1/2020 | Lowry et al. |
| 2020/0157093 A1 | 5/2020 | Lowry et al. |
| 2020/0253917 A1 | 8/2020 | Lowry et al. |

FOREIGN PATENT DOCUMENTS

| | | |
|---|---|---|
| WO | WO-9200057 A1 | 1/1992 |
| WO | WO-1992/007839 A1 | 5/1992 |
| WO | WO-0162237 A2 | 8/2001 |
| WO | WO-2004080481 A1 | 9/2004 |
| WO | WO-2007099396 A2 | 9/2007 |
| WO | WO-2013128465 A1 | 9/2013 |
| WO | WO-2013/169956 A2 | 11/2013 |
| WO | WO-2014/207213 A1 | 12/2014 |
| WO | WO-2015/049365 A2 | 4/2015 |
| WO | WO-2018039612 A1 | 3/2018 |
| WO | WO-2019/006359 A1 | 1/2019 |
| WO | WO-2020/142413 A1 | 7/2020 |

OTHER PUBLICATIONS

Amin et al., "Exploring structural requirements of unconventional Knoevenagel-type indole derivatives as anticancer agents through comparative QSAR modeling approaches," Can J Chemistry, 94(7):637-644 (2016).
CAS Registry No. 1025594-30-2, Entered STN:Jun. 5, 2008.
CAS Registry No. 1232821-01-0, Entered STN:Jul. 19, 2010.
CAS Registry No. 1246086-21-4, Entered STN:Oct. 12, 2010.
CAS Registry No. 1360583-75-0, Entered STN:Mar. 9. 2012.
CAS Registry No. 1360583-78-3, Entered STN:Mar. 9, 2012.
CAS Registry No. 1417368-01-4, Entered STN:Jan. 23, 2013.
CAS Registry No. 1993738-37-6, Entered STN:Sep. 16, 2016.
CAS Registry No. 1993795-68-8, Entered STN:Sep. 16, 2016.
CAS Registry No. 2022941-63-3, Entered STN:Nov. 2, 2016.
CAS Registry No. 2094959-90-5, Entered STN:May 5, 2017.
CAS Registry No. 677327-34-3, Entered STN:Apr. 28, 2004.
CAS Registry No. 895303-82-9, Entered STN:Jul. 23, 2006.
CAS Registry No. 895304-22-0, Entered STN:Jul. 23, 2006.
CAS Registry No. 904141-89-5, Entered STN: Aug. 24, 2006.
Flores et al., "Lactate dehydrogenase activity drives hair follicle stem cell activation," Nat Cell Biol, 19:1017-1026 (2017).
International Search Report and Written Opinion for International Application No. PCT/US2017/048701 dated Nov. 6, 2017.
International Search Report and Written Opinion for International Application No. PCT/US2018/040385 dated Oct. 21, 2018.
International Search Report and Written Opinion for International Application No. PCT/US2018/053351 dated Dec. 31, 2018.
Liu et al., "Identification of novel thiadiazoloacrylamide analogues as inhibitors of dengue-2 virus NS2B/NS3 protease," Bioorg Med Chem, 22(22):6344-6352 (2014).
McCommis et al., "Mitochondrial pyruvate transport: a historical perspective and future research directions," Biochem J, 466(3):443-454 (2015).
Vishnyakova et al., "Possible role of autophagy activation in stimulation of regeneration," Mol Biol, 47(5):692-00 (2013).
Flores et al., "Lactate dehydrogenase activity drives hair follicle stem cell activation," Nature Cell Biology, 19(9): 1017-1026 (2017).
International Search Report and Written Opinion for International Application No. PCT/US2019/068905 dated Apr. 6, 2020.
Jelinek et al., "Mapping Metabolism: Monitoring Lactate Dehydrogenase Activity Directly in Tissue," Journal of Visualized Experiments, 136: 57760 (2018).
Miranda et al., "Topical Inhibition of the Electron Transport Chain Can Stimulate the Hair Cycle," Journal of Investigative Dermatology, 138: 968-972 (2018).
International Preliminary Report on Patentability for International Application No. PCT/US2018/040385 dated Dec. 31, 2019.
Yakhontov et al., "Pyrrolo[2,3-b]pyridine derivatives (7-azaindoles) viii. Synthesis and some reactions of 4-methyl-1-phenyl-1h-4-methyl-1-phynyl-1 h-pyrrol0[2,3-b]pyridine-3-carboxaldehydel," All-Union Chem Pharma Res Int, translated from Zhurnal Obshchei Khimii 34(8):2603-2610 (1964).
Extended European Search Report for EP Application No. 17844520.1 dated Jul. 21, 2020.
U.S. Appl. No. 16/627,630, Pending.
U.S. Appl. No. 16/651,835, Pending.
U.S. Appl. No. 16/415,822, Pending.
Choi et al., "The effect of cilostazol, a phosphodiesterase 3 (PDE3) inhibitor, on human hair growth with the dual promoting mechanisms," Journal of Dermatological Science, 91: 60-68 (2018).
Fischer et al., "Effect of caffeine and testosterone on the proliferation of human hair follicles in vitro ," International Journal of Dermatology, 46: 27-35 (2007).
Keren et al., "The PDE4 inhibitor, apremilast, suppresses experimentally induced alopecia areata in human skin in vivo," Journal of Dermatological Science, 77: 71-81 (2015).
Sarifakioglu., "Determination of the sildenafil effect on alopecia areata in childhood: An open-pilot comparison study," Journal of Dermatological Treatment, 17(4): 235-237 (2006).
Taylor et al., "Src tyrosine kinsase activity in rat thecal—interstitial cells and mouse TM3 Leydig cells is positively associated with cAMP-specific phosphodiesterase activity," Molecular and Cellular Endocrinology, 126: 91-100 (1997).

\* cited by examiner

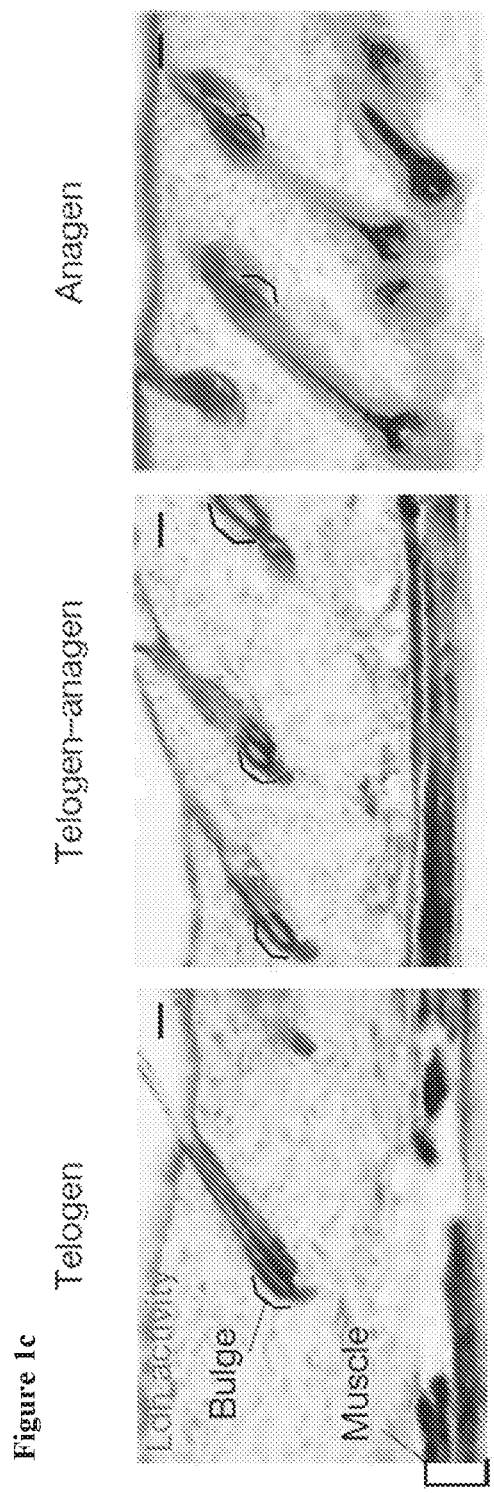

COMPOSITIONS AND METHODS FOR PROMOTING HAIR GROWTH WITH MPC1 INHIBITORS

RELATED APPLICATIONS

This application is the U.S. National Stage of PCT/US2017/048701, filed Aug. 25, 2017, which claims the benefit of priority to U.S. Provisional Patent Application Ser. No. 62/463,232, filed Feb. 24, 2017.

The contents of PCT/US2017/048701, and U.S. Provisional Patent Application Ser. Nos. 62/380,205 and 62/463,232 are hereby incorporated by reference herein in their entireties.

BACKGROUND

More than 400 million people worldwide have baldness. Male pattern baldness affects about 50% of the male population aged 50 and above. Available hair growth treatments produce short, fuzzy hairs and require continuous application. That is, once treatment stops, new hair growth ends and hair loss resumes.

Two drugs currently approved by the Food & Drug Administration (FDA) for the treatment of baldness are ROGAINE® (topical minoxidil) and PROPECIA® (oral finasteride). Minoxidil is the only FDA approved medication to treat female pattern baldness, but it only works for top of head hair loss. Finasteride is used in men only because it can cause birth defects in pregnant women. Finasteride also has adverse effects on sexual health.

There is a need for improved compositions and methods of accelerating, promoting, or restoring hair growth with fewer adverse effects.

SUMMARY

One aspect of the disclosure relates to methods of accelerating, promoting, or restoring hair growth, comprising administering to a subject in need thereof an effective amount of a compound of formula (I):

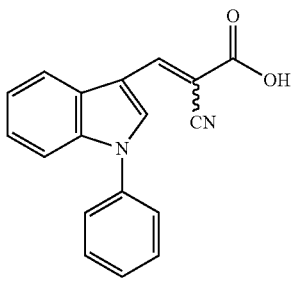

(I)

or a pharmaceutically acceptable salt thereof.

In some embodiments, disclosed herein are methods of treating a condition selected from alopecia, hair loss, hair thinning, and baldness.

Another aspect of the disclosure relates to compositions comprising a compound of formula (I):

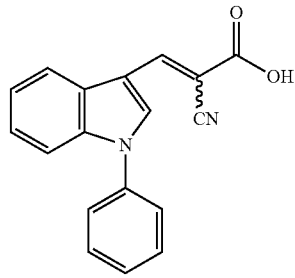

(I)

or a pharmaceutically acceptable salt thereof, and a carrier or excipient suitable for topical application to skin.

In some embodiments, disclosed herein the compositions may be used in the manufacture of a medicament for the treatment of a condition as described herein.

BRIEF DESCRIPTION OF THE DRAWINGS

FIG. 1c, colorimetric assay for Ldh enzyme activity in the epidermis shows highest activity in the bulge (brackets) and subcuticular muscle layer (bracket). This activity was enriched in the bulge across different stages of the hair cycle. Activity is indicated by dark color; gray is a nuclear counterstain. Note also that developing hair shafts in pigmented mice show strong deposits of melanin as observed here; hair shafts never displayed any dark stain indicative of Ldh activity.

FIG. 3l, Metabolomic analysis of lactate on HFSCs isolated from compound of formula (I)-treated skin for 48 hours.

FIG. 4l, Deletion of Mpc1 in mice bearing the Lgr6CreER allele shows no premature induction of the hair cycle.

DETAILED DESCRIPTION

Hair follicle stem cells (HFSCs) are quiescent, long-lived cells that are responsible for maintaining the cellular homeostasis of the follicle. While normally dormant, HFSCs quickly become activated to divide during a new hair cycle. The quiescence of HFSCs is known to be regulated by a number of intrinsic and extrinsic mechanisms.

Figure 1A:
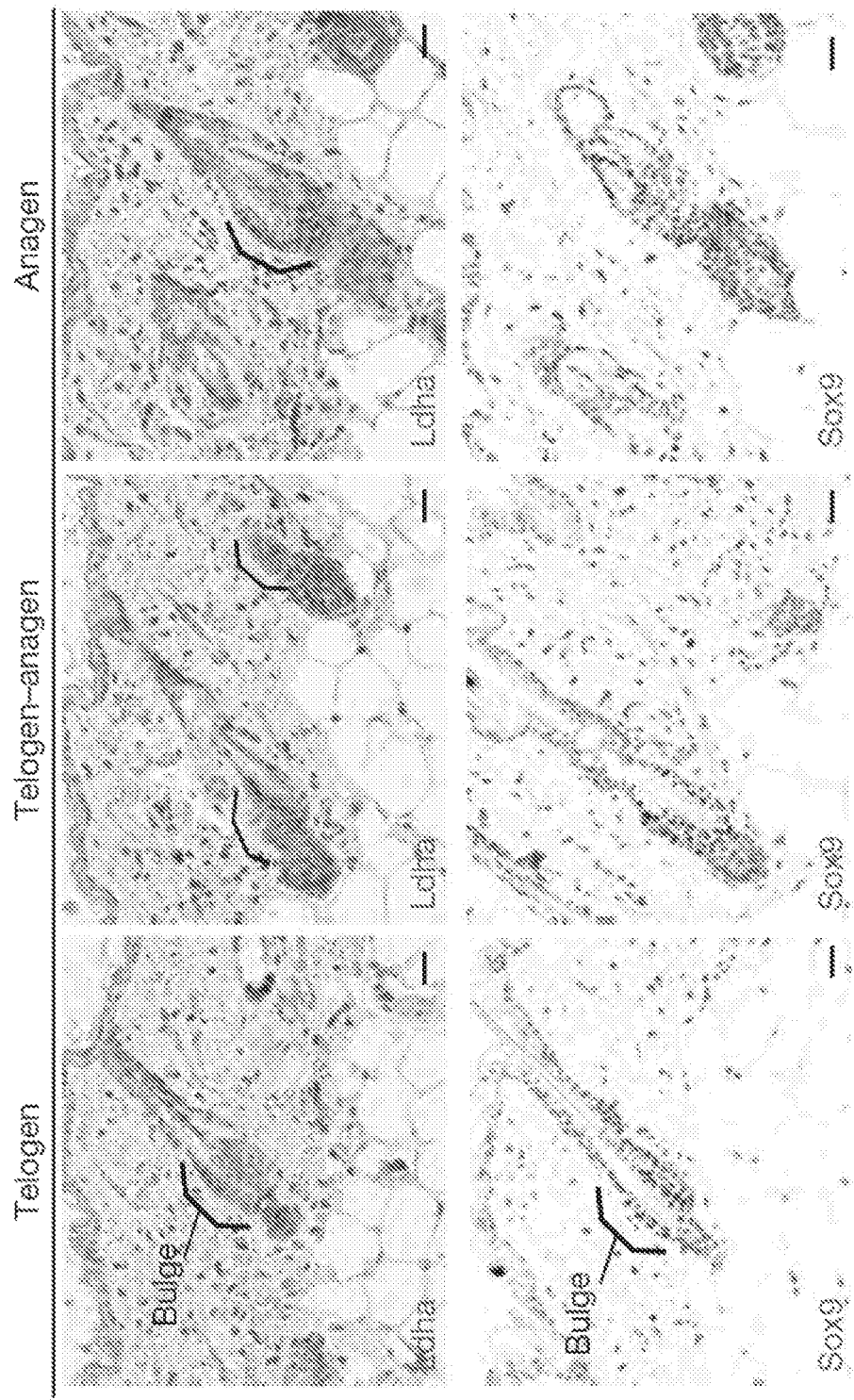
FIG. 1a shows Lactate Dehydrogenase activity was enriched in the Hair Follicle Stem Cell niche. Immunohistochemistry (IHC) staining for Ldha expression across the hair cycle shows Ldha protein confined to the hair follicle stem cell (HFSC) niche, the bulge, indicated by the bracket. IHC staining for total Ldh in epidermis shows expression in interfollicular epidermis, infundibulum, sebaceous gland and hair follicle bulge, shown in bracket. IHC staining for Sox9 on serial sections demarcates the HFSC population. Scale bars, 20 µm.

The hair follicle is able to undergo cyclical rounds of rest (telogen), regeneration (anagen), and degeneration (catagen). The ability of the hair follicle to maintain this cycle depends on the presence of the hair follicle stem cells, which reside in the bulge (FIG. 1a). At the start of anagen, bulge stem cells are activated by signals received from the dermal papilla, which at that stage abuts the bulge area. These stem cells exit the bulge and proliferate downwards, creating a trail that becomes the outer root sheath (ORS). Bulge stem cells are capable of giving rise to all the different cell types of the hair follicle. The ability of HFSCs to maintain quiescence and yet become proliferative for a couple days before returning to quiescence is unique in this tissue.

HFSCs display an ability to shuttle back and forth between proliferative and quiescent states in vivo during the hair cycle[1,2]. New methods to study the metabolism of HFSCs in vivo are provided herein. Evidence is provided that these cells require glycolysis and lactate dehydrogenase activity to allow for their reactivation after extended periods of dormancy. Furthermore, these findings were used to uncover novel pharmacological methods to promote HFSC activation and the hair cycle.

Methods of Use

In one aspect, the disclosure provides methods of accelerating, promoting, or restoring hair growth, comprising administering to a subject in need thereof an effective amount of a compound of formula (I):

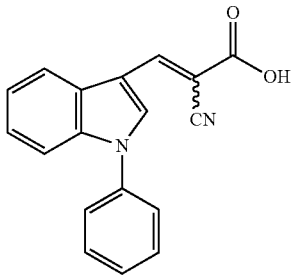

(I)

or a pharmaceutically acceptable salt thereof.

The phrase "restoring hair growth" as used herein, means improving hair growth. For example, this includes proliferation or activation of hair follicle stem cells, e.g., shifting hair follicles from the resting phase to active growth phase. In addition, when a subject exhibits symptoms, such as alopecia, hair loss, hair thinning, and baldness, treatment with a compound or composition disclosed herein reduces these symptoms compared to before treatment. In some embodiments, restoring hair growth is measured relative to the absence of administration of the compound of formula (I).

Non-limiting examples of improvements in hair growth correlated to accelerating, promoting, or restoring hair growth can be selected from:
(a) improvement in root sheath thickness:
(b) improvement in hair anchorage:
(c) decrease in hair loss;
(d) reduction in hair breakage;
(e) increase in hair strength;
(f) improvement in hair growth rate;
(g) improvement in shine;
(h) improvement in the number of visible hair strands;
(i) improvement in hair length;
(j) improvement in hair strand volume;
(k) shift from telogen phase to anagen phase;
(l) entry into a new hair cycle;
(m) increase in hair follicles in the growth phase;
(n) increase in hair follicle stem cell (HFSC) activation;
(o) activate a quiescent HFSC:
(p) increase glycolysis in a HFSC;
(q) activate lactate dehydrogenase in a HFSC.

In some embodiments, administering comprises topically applying a composition comprising the compound to an affected area.

In some embodiments, the subject exhibits symptoms selected from alopecia, hair loss, hair thinning, and baldness. In some embodiments, the subject exhibits symptoms selected from hair loss, hair thinning, and baldness.

In some embodiments, the subject exhibits baldness. In some embodiments, the baldness is male pattern baldness or female pattern baldness.

In some embodiments, the subject exhibits symptoms selected from hair loss and hair thinning. In some embodiments, the hair loss or the hair thinning is caused by anagen effluvium or telogen effluvium.

In some embodiments, anagen effluvium is triggered by chemotherapy (e.g., cytostatic drugs) and ingesting toxic products (e.g., rat poison).

In some embodiments, telogen effluvium is triggered by stress (e.g., vaccinations, physical trauma (including a car crash, surgery, and giving birth), chronic illness, and certain medications including antidepressants) and diet (e.g., lack of iron, excessive iron, lack of zinc, lack of L-lysine, lack of vitamin B6, lack of vitamin B12, and excessive vitamin A).

In some embodiments, the hair loss or the hair thinning is caused by an autoimmune disorder.

In some embodiments, the alopecia is selected from juvenile alopecia, premature alopecia, senile alopecia, alopecia areata, androgenic alopecia, mechanical alopecia, postpartum alopecia, and symptomatic alopecia.

In some embodiments, the compound is applied to a hair follicle.

In some embodiments, the compound of formula (I) is used in the manufacture of a medicament for the treatment of any symptoms or conditions disclosed herein.

In some embodiments, the condition is slowing or stopping hair growth. In some embodiments, the condition of slowing or stopping hair growth is selected from alopecia, hair loss, hair thinning, and baldness. In some embodiments, the condition selected from alopecia, hair loss, hair thinning, and baldness.

In some embodiments of the methods disclosed herein, the method comprises activating a quiescent HFSC. In some embodiments, the quiescent HFSC is in a subject. In some embodiments, the quiescent HFSC is in a human subject.

In some embodiments of the methods disclosed herein, the method comprises increasing glycolysis in a HFSC. In some embodiments, levels of glycolytic metabolites are increased relative to the absence of administration of the compound of formula (I). In some embodiments, the glycolytic metabolites are selected from glucose; G6P, glucose-6-phosphate, F6P, fructose-6-phosphate; FBP, fructose-bisphosphate; DHAP, dihydroxyacetone phosphate; 3PG, 3-phosphoglycerate; 3PL, 3-phospholactate; and αKG, alphaketoglutarate. In some embodiments, the glycolytic metabolites are selected from glucose; G6P; F6P; FBP; DHAP; 3PG; and 3PL.

In some embodiments of the methods disclosed herein, the method comprises activating lactate dehydrogenase in a HFSC.

In some embodiments of the methods disclosed herein, the HFSC is a human HFSC. In some embodiments, the HFSC is within a human subject.

Compositions

In another aspect, the present disclosure provides a pharmaceutical composition comprising a compound of formula (I), optionally admixed with a pharmaceutically acceptable carrier or diluent.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, the compound of formula (I) of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, cream, lotion or the like. The composition can also be present in a transdermal delivery system, e.g., a skin patch. The composition can also be present in a solution or composition suitable for topical administration.

In some embodiments, the present disclosure provides a composition comprising a compound of formula (I):

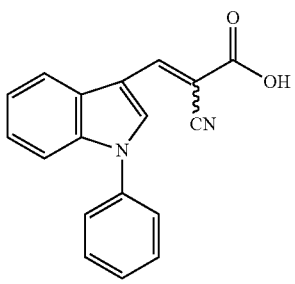

(I)

or a pharmaceutically acceptable salt thereof, and a carrier or excipient suitable for topical application to skin.

In some embodiments, the carrier or excipient is generally safe and non-irritating when applied to skin, in particular, for application to hair or scalp.

A pharmaceutically acceptable carrier can contain physiologically acceptable agents that act, for example, to stabilize, increase solubility or to increase the absorption of a compound such as the compound of formula (I) of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation of composition can be a self-emulsifying drug delivery system or a self-microemulsifying drug delivery system. The composition (preparation) also can be a liposome or other polymer matrix, which can have incorporated therein, for example, the compound of formula (I) of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, soybean oil (e.g., *Glycine soja* oil), linseed oil (e.g., *Linum usitatissium* seed oil), and eucalyptus oil (e.g., *Eucalyptus globulus* leaf oil); (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide: (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In some embodiments, the carrier is selected from polyols (e.g., propylene glycol, butylene glycol, pentylene glycol, hexylene glycol, caprylyl glycol, and glycerin), carbitol, glycol ethers (e.g., ethylene glycol monobutyl ether, propylene glycol monomethyl ether, propylene glycol monobutyl ether, dipropylene glycol and diethylene glycol), alkyl ethers (e.g., diethylene glycol monoethyl ether (ethoxy diglycol) and diethylene glycol monobutyl ether), pyrogen-free water, alcohol (e.g., ethyl alcohol, isopropanol, propanol, butanol, benzyl alcohol, and phenylethyl alcohol).

In some embodiments, the composition is an emulsion. Emulsions include oil-in-water, silicone-in-water, water-in-oil, water-in-silicone, and the like. When formulated as an emulsion, an emulsifier is typically included.

In some embodiments, the composition further comprises an ingredient selected from a surfactant, a thickener, a fragrance, a UV-screening agent, a wax, a silicone, a preservative, an oil, a vitamin, a provitamin, an opacifier, an antioxidant, an emulsifier, an excipient, a solvent, and a buffer. Examples of the foregoing agents may be found in the International Cosmetic Ingredient Dictionary and Handbook, Twelfth Ed., 2008 or online (herein incorporated by reference in its entirety).

Examples of a surfactant include, but are not limited to, oleth 5, oleic acid, sodium dodecyl sulfate, sodium lauryl sulfate, and poloxamer 407.

Examples of a thickener include, but are not limited to, fatty alcohols (e.g., cetyl alcohol and oleyl alcohol), ethoxylated phenols (e.g., octoxynol-1, nonoxynol-4, and nonoxynol-9), and polymers (e.g., hydroxyethylcellulose and hydroxypropyl methylcellulose).

Examples of a UV-screening agent include, but are not limited to, avobenzone, benzophenone-4, oxybenzone, octinoxate, titanium dioxide, and zinc oxide.

Examples of a wax include, but are not limited to, beeswax, candelilla wax, carnauba wax, and castor wax.

Examples of a preservative include, but are not limited to, isothiazolinones, parabens, phenoxyethanol, benzoic acid, sodium benzoate, sorbic acid, and potassium sorbate.

Examples of an oil include, but are not limited to, avocado oil, coconut oil, linseed oil, peanut oil, cottonseed oil, safflower oil, sesame oil, olive oil, corn oil and soybean oil.

Examples of a vitamin include, but are not limited to, vitamin E, vitamin C, vitamin B.

Examples of pharmaceutically acceptable antioxidants include, but are not limited to:

(1) water-soluble antioxidants, such as ascorbic acid, erythorbic acid, and isoascorbic acid cysteine hydrochloride, sodium bisulfate, sodium metabisulfite, sodium sulfite and the like, (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Examples of an emulsifier include, but are not limited to, ceteareth-20, ceteareth-25, cetearyl alcohol, lechithin, glyceryl stearate, sorbitan stearate, glyceryl oleate, polyglyceryl oleate, sorbitan oleate, isopropyl palmitate, polysorbate 20, polysorbate 60, polysorbate 80, stearic acid, and cetyl phosphate.

In some embodiments, the composition is applied in a form selected from a shampoo, a hair rinse, a hair conditioner, a pomade, a hair gel, a mousse, a hydroalcoholic tonic, a cream, a spray, an emulsion, and a liquid.

In some embodiments, the composition is an emulsion comprising water and stearic acid. In some embodiments, the composition is an emulsion comprising a pharmaceutically acceptable carrier, an emulsifier, an oil, and a fragrance. In some embodiments, the composition is an emulsion comprising water, propylene glycol, gelatin, stearic acid, linseed oil, soybean oil, eucalyptus oil, and a fragrance.

In some embodiments, the composition is an emulsion comprising pluronic lecithin organogel. In some embodiments, the composition is an emulsion comprising water, poloxamer (e.g., poloxamer 407), and lecithin. In some embodiments, the composition is an emulsion comprising water, poloxamer (e.g., poloxamer 407), lecithin, and ethoxy diglycol. In some embodiments, the composition is an emulsion comprising water, poloxamer 407, potassium sorbate, lecithin, isopropyl palmitate, and sorbic acid. In some embodiments, the composition is an emulsion comprising water, poloxamer 407, potassium sorbate, lecithin, isopropyl palmitate, sorbic acid, and ethoxy diglycol. In some embodiments, the composition is an emulsion comprising PLO gel or PLO Ultramax gel.

A composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); transdermally (for example as a patch applied to the skin); and topically (for example, as a cream, ointment or spray applied to the skin, or as a product applied to the hair). In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 0.001 percent to about 99 percent of active ingredient. In some embodiments, this amount will range from about 5 percent to about 70 percent. In some embodiments, this amount will range from about 10 percent to about 30 percent. In some embodiments, this amount will range from about 0.001 percent to about 10 percent by weight of the composition.

Methods of preparing these formulations or compositions include the step of bringing into association an active compound, such the compound of formula (I) of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as a wetting agent, an emulsifier, a suspending agent, a sweetener, a flavor, a dye, a fragrance, and a preservative.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, and patches. The active compound may be mixed under sterile conditions with a pharmaceutically acceptable carrier, and with any preservatives, buffers, or solvents that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Examples of suitable aqueous and nonaqueous carriers that may be employed in the compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifiers and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

The pharmaceutical compositions may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212, 162; and 4,861,760. The entire contents of these patents are incorporated herein by reference in their entirety for all purposes.

For use in the methods of this disclosure, active compounds can be given per se or as a composition containing, for example, 0.001 to 99.5% (more preferably, 0.001 to 10%) of active ingredient in combination with a pharmaceutically acceptable carrier.

Actual dosage levels of the active ingredients in the compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the composition required. For example, the physician or veterinarian could start doses of the composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight sex, age, and medical history of the subject. Other factors which influence the effective amount may include, but are not limited to, the severity of the patient's condition, the disorder being treated, the stability of the compound, and, if desired, another type of therapeutic agent being administered with the compound of formula (I) of the disclosure. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In some embodiments of the present disclosure, the active compound may be administered two or three times daily. In some embodiments, the active compound will be administered once daily.

The patient receiving this treatment is any animal in need, including primates, in particular humans, and other mammals such as equines, cattle, swine and sheep; and poultry and pets in general.

The invention now being generally described, it will be more readily understood by reference to the following examples which are included merely for purposes of illustration of certain aspects and embodiments of the present invention, and are not intended to limit the invention.

EXAMPLES

Abbreviations

ACN acetonitrile
AEC 3-amino-9-ethylcarbazole
BCA bicinchoninic assay
BCS bovine calf serum
DMSO dimethyl sulfoxide
FACS fluorescence-activated cell sorting
HFSC hair follicle stem cell
Hk hexokinase
Ldh lactate dehydrogenase
Ldha lactate dehydrogenase A
Ldha lactate dehydrogenase B
NAD β-nicotinamide adenine dinucleotide
NADH reduced β-nicotinamide adenine dinucleotide
OCT optimal cutting temperature medium
PBS phosphate buffered saline
PLO pluronic lecithin organogel
p-S6 phospho-S6 ribosomal protein
p-Stat3 phospho-signal transducer and activator of transcription 3
RIPA radioimmunoprecipitation assay
TCA cycle tricarboxylic acid cycle
XTT 2,3-bis (2-methoxy-4-nitro-5-sulfophenyl)-2H-tetrazolium-5-carboxanilide
Materials and Methods
  Mice
  Animals were acquired from Jackson Labs (K15-CrePR, Lgr5-CreER and Lgr6-CreER), Rutter Lab (Mpc$^{fl/fl}$) and Seth Lab (Ldha$^{fl/fl}$) (Xie, H. et al., *Cell Metab.*, 19, 795-809 (2014)) and maintained under conditions set forth by IUCUC and ARC. For experiments that include analysis of the telogen stage of the hair cycle, animals were harvested at post-natal day 50, for telogen-anagen transition animals were harvested at day 70, and for anagen animals were harvested at post-natal day 90. For experiments that include analysis of transgenic animals, K15-CrePR animals were shaved and treated by intraperitoneal injections of mifepristone and Lgr5-CreER and Lgr6-CreER animals were shaved and treated with tamoxifen (10 mg/ml dissolved in sunflower seed oil, 2 mg per day for 3 days) during telogen (post-natal day 50), and monitored for hair regrowth following shaving. Phenotypes shown from treated animals were produced 3-4 weeks after mifepristone administration. For FIG. 3, wildtype C57BL/6J animals were shaved at post-natal day 50 and treated topically with Transderma PLO Gel (premium lecithin organogel), PLO Gel Ultramax Base (TR220) (vehicle), or the compound of formula (I) (Compound (I)) (20 µM) (Sigma Aldrich product PZ0160) for indicated periods of time. Both male and female animals were used in this study in approximately equal numbers with no apparent difference in phenotype between genders. All phenotypes described are representative of a minimum of n=3 littermate pairs as indicated in the description of each experiment. No statistical measure was used to determine the sample size beforehand, nor were statistics used to measure effects, as the results were essentially positive or negative as represented in the figures. The results described include data from all treated animals. The investigators were not blinded to allocation during the experimental data collection, nor were the experiments randomized. The results shown were representative images from at least three independently treated animals, and genotyping was performed both before and after animal treatment for confirmation.

Histology, Immunostaining, and Immunoblotting
  Tissues were isolated from the indicated genotypes and embedded fresh in optimal cutting temperature (OCT) compound for frozen tissue preparations, or fixed overnight in 4% formalin and embedded in paraffin. For frozen tissue, sectioning was performed on a Leica 3200 Cryostat, and fixed for 5 minutes in 4% paraformaldehyde. Paraffin embedded tissue was sectioned, de-paraffinized, and prepared for histology. All sections prepared for staining were blocked in staining buffer containing appropriate control IgG (Goat, Rabbit etc.). Immunohistochemistry was performed on formalin-fixed paraffin-embedded tissue with citrate or Tris buffer antigen retrieval with the following antibodies: Ki67 (Abcam ab16667, 1:50), p-S6 (Cell Signaling CST2215, 1:50), Sox9 (Abcam ab185230, 1:1000), Ldha (Abcam ab47010, 1:100), Ldh (Abcam ab125683, 1:100), p-Stat3 (Abcam ab68153, 1:200), p-Stat1 (Abcam ab109461, 1:200), p-Stat5 (Abcam ab32364; 1:50), Gli3 (Abcam ab6050; 1:100), β-catenin (Abcam ab32572; 1:500). The DAKO EnVision+ HRP Peroxidase System (Dako K400911-2) and Dako AEC Substrate Chromogen (Dako K346430-2) was used for detection. Images were collected on an Olympus BX43 Upright Microscope and Zeiss Model Axio Imager M1 Upright Fluorescence Microscope. Protein samples for western blots and enzymatic assays were extracted from FACS sorted epidermal populations in RIPA lysis buffer (Pierce) with Halt protease and phosphatase inhibitors (Thermo-Fisher) and precipitated in acetone for concentration. The following antibodies were used: β-actin (Abcam ab8227; 1:1000), β-actin (Santa Cruz sc-47778; 1:1000), C-Myc (Abcam ab32072; 1:1000), N-Myc (Santa Cruz sc-53993; 1:200), H3K27Ac (Abcam ab177178; 1:200), Mpc1 (Sigma HPA045119).

Cell Isolation and FACS
  Whole dorsal and ventral mouse skin were excised and floated on trypsin (0.25%) for 1 h at 37° C. or overnight at 4° C. The epidermis was separated from dermis by scraping and epidermal cells were mechanically dissociated using a pipette. Epidermal cells were filtered with a 70 µM cell strainer into 20% bovine calf serum (BCS), collected at 300 g and washed twice with phosphate buffered saline (PBS). The cells were then filtered through a 40 μM cell strainer and stained for fluorescence-activated cell sorting (FACS) processing with CD34 Monoclonal Antibody (RAM34), FITC, eBioscience™ (Catalog #:11-0341-82) and CD49d (Integrin alpha 4) Monoclonal Antibody (R1-2), PE, eBioscience™ (Catalog #: 12-0492-81). Gating strategy shown in FIG. 4a. Cells sorted using BD FACSAria high-speed cell sorters. Single positive and double positive populations were collected into 20% BCS. RIPA lysis buffer (Thermo Scientific, Pierce), or 80% methanol for enzymatic assays, western blots or mass spec analyses respectively.

Plate-Reader Ldh Assay

Ldh activity was determined in cell lysates by measuring the formation of soluble 2,3-bis (2-methoxy-4-nitro-5-sulfophenyl)-2H-tetrazolium-5-carboxanilide (XTT) formazan in direct relation to production of NADH over time at 475 nm at 37° C. using a Synergy-MX plate reader (Biotek Instruments). Lysates were prepared in radioimmunoprecipitation assay (RIPA) Buffer (Thermo Scientific Pierce). Protein content was determined using the bicinchoninic assay (BCA) Protein Assay Kit (Thermo Scientific Pierce), 10 μg of protein were used per well. The staining solution contained 50 mM Tris buffer pH 7.4, 150 μM XTT (Sigma), 750 μM f-nicotinamide adenine dinucleotide (NAD) (Sigma), 80 μM phenazine methosulfate (Sigma) and 10 mM of substrate lactate (Sigma). Ldh activity was determined in cell lysates by measuring the change in absorbance of their common substrate or product, reduced β-nicotinamide adenine dinucleotide (NADH), over time at 340 nm at 25° C. using a Synergy-MX plate reader (Biotek Instruments).

In Situ Ldh Assay

Cryostat sections of mouse skin were briefly fixed (4% formalin for 5 min), washed with PBS pH 7.4, and then incubated with the appropriate solution for LDH activity. Staining medium contained 50 mM Tris pH 7.4, 750 μM NAD (Sigma), 80 μM phenazine methosulfate (Sigma), 600 μM Nitrotetrazolium Blue chloride (Sigma), 10 mM MgCl2 (Sigma) and 10 mM of the substrate lactate (Sigma). Slides were incubated with staining medium at 37° C. until they reached the desired intensity, then counterstained using Nuclear Fast Red (Vector, Burlingame, Calif.) and mounted using VectaMount (Vector, Burlingame, Calif.). Control reactions were performed by using incubation medium that lacked the substrate mixture or NAD.

Mass Spectrometry-Based Metabolomics Analysis

The experiments were performed as described in Folmes, C. D. et al. Somatic oxidative bioenergetics transitions into pluripotency-dependent glycolysis to facilitate nuclear reprogramming. *Cell Metab* 14, 264-271. To extract intracellular metabolites, FACS sorted cells were briefly rinsed with cold 150 mM ammonium acetate (pH 7.3), followed by addition of 1 ml cold 80% methanol (MeOH) on dry ice. Cell suspensions were transferred into Eppendorf tubes and 10 nmol D/L-norvaline was added. After rigorously mixing, the suspension was pelleted by centrifugation ($1.3*10^4$ rpm, 4° C.). The supernatant was transferred into a glass vial, metabolites dried down under vacuum, and resuspended in 70% acetonitrile. For the mass spectrometry-based analysis of the sample, 5 μl were injected onto a Luna NH2 (150 mm×2 mm, Phenomenex) column. The samples were analyzed with an UltiMate 3000RSLC (Thermo Scientific) coupled to a Q Exactive mass spectrometer (Thermo Scientific). The Q Exactive was run with polarity switching (+3.50 kV/−3.50 kV) in full scan mode with an m/z range of 65-975. Separation was achieved using A) 5 mM ammonium acetate ($NH_4AcO$) (pH 9.9) and B) acetonitrile (ACN). The gradient started with 15% A) going to 90% A) over 18 min, followed by an isocratic step for 9 min and reversal to the initial 15% A) for 7 min. Metabolites were quantified with TraceFinder 3.3 using accurate mass measurements (≤3 ppm) and retention times.

Statistics

Both male and female animals were used in this study in approximately equal numbers with no apparent difference in phenotype between genders. All phenotypes described are representative of a minimum of n=3 littermate pairs as indicated in the description of each experiment. For analysis of hair regrowth phenotype no statistical measure was used to determine the sample size beforehand, nor were statistics used to measure effects, as the results were essentially positive or negative as represented in the figures. The results described include data from all treated animals. The investigators were not blinded to allocation during the experimental data collection, nor were the experiments randomized. All results shown were representative images from at least three independently treated animals, and genotyping was performed both before and after animal treatment for confirmation. For graphs, all comparisons are shown by Student's two-tailed unpaired t-test and all graphs, bars or lines indicate mean and error bars indicate Standard error of the mean (s.e.m).

Figure 4A:
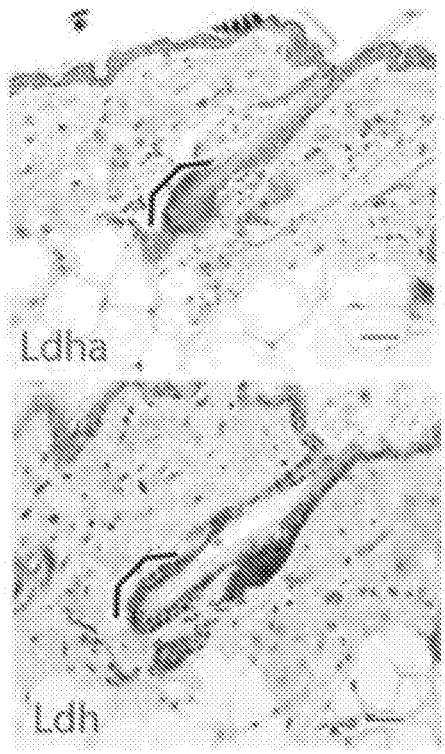
FIG. 4a shows the sorting strategy employed to isolate two populations of cells from the bulge. This particular sort was used to isolate the protein samples shown by western blot in FIG. 1d.

Example 1: Lactate Dehydrogenase Activity is Enriched in the Hair Follicle Stem Cell Niche Numerous studies have uncovered unique gene expression signatures in HFSCs versus other follicle cells or cells of the interfollicular epidermis[3-6]. Many of these signatures are regulated by transcription factors that were later shown to play important roles in HFSC homeostasis[7]. Lactate dehydrogenase is most commonly encoded by the Ldha and Ldhb genes in mammals, the protein products of which form homo- or hetero-tetramers to catalyze the NADH-dependent reduction of pyruvate to lactate and $NAD^+$-dependent oxidation of lactate to pyruvate[9]. By immunostaining, Ldha appeared to be enriched in quiescent HFSCs in situ (telogen) (FIG. 1a), IHC with an antibody that recognizes Ldha and Ldhb showed that only Ldha appears to be localized to the HFSC niche (FIG. 4a).

Figure 1B:
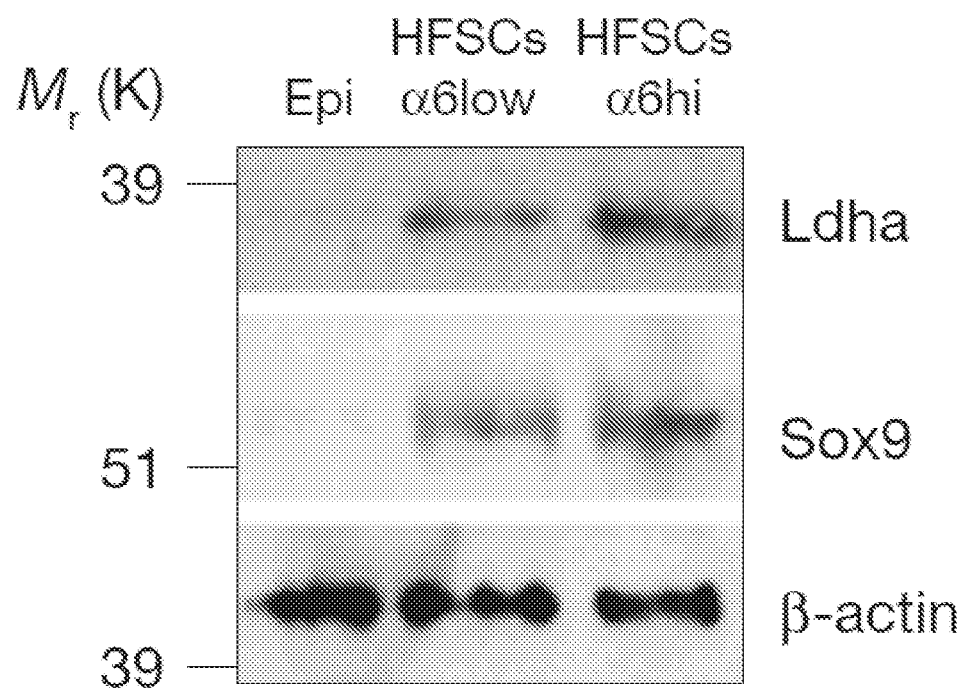
FIG. 1b, immunoblotting on FACS-isolated HFSC populations (α6low/Cd34$^+$ and α6hi/Cd34$^+$) versus total epidermis (Epi) shows differential expression of Ldha in the stem cell niche. Sox9 is a marker of HFSCs, and β-actin is a loading control.
Figure 4B:
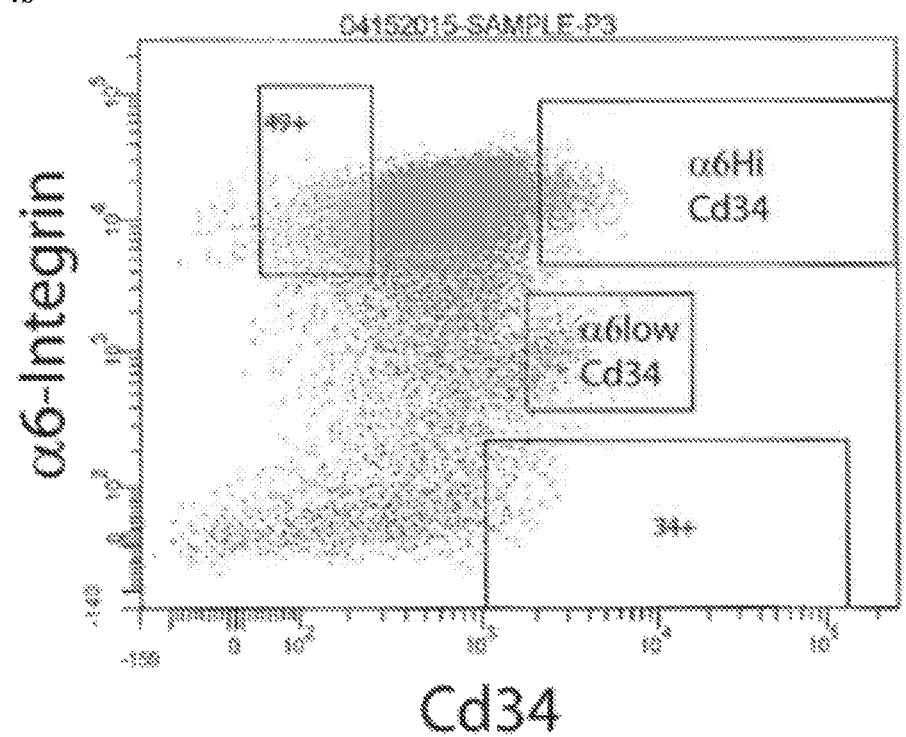
FIG. 4b shows immunohistochemistry (IHC) staining (top) with antibody recognizing specifically Ldha and (bottom) with antibody recognizing multiple isoforms of lactate dehydrogenase (Ldh) protein. Scale bars, 20 µm.

HFSCs are known to go through successive rounds of quiescence (telogen) punctuated by brief periods of proliferation correlating with the start of the hair cycle (telogen-anagen transition). Proliferation or activation of HFSCs is well known to be a prerequisite for advancement of the hair cycle. IHC analysis also showed Ldha expression was enriched in HFSCs (Sox9+) at three stages of the hair cycle (FIG. 1a). Consistently, immunoblotting of lysates from sorted cells showed nearly exclusive expression of Ldha in the basal HFSCs (α6HiCD34+), and significantly more Ldhb in both the basal (α6HiCD34+) and suprabasal (α6LoCD34+) HFSC populations relative to total epidermis (FIG. 1b)[3]. Sorting strategy is outlined in FIG. 4b.

To determine whether Ldha expression patterns correlate with activity of the Ldh enzyme, a colorimetric-based enzymatic assay was used to assess Ldh activity capacity in situ. Typically performed on protein lysates or aliquots with a plate reader (Nguyen, H., et al., *Cell*, 127, 171-183 (2006)), the Ldh activity assay was adapted to work in situ on frozen tissue sections. Note that since both the in situ and in vitro Ldh activity assays employ use of excess substrate (lactate), the results from these assays reflect the capacity for Ldh activity, and not the steady-state activity.

Figure 1D:
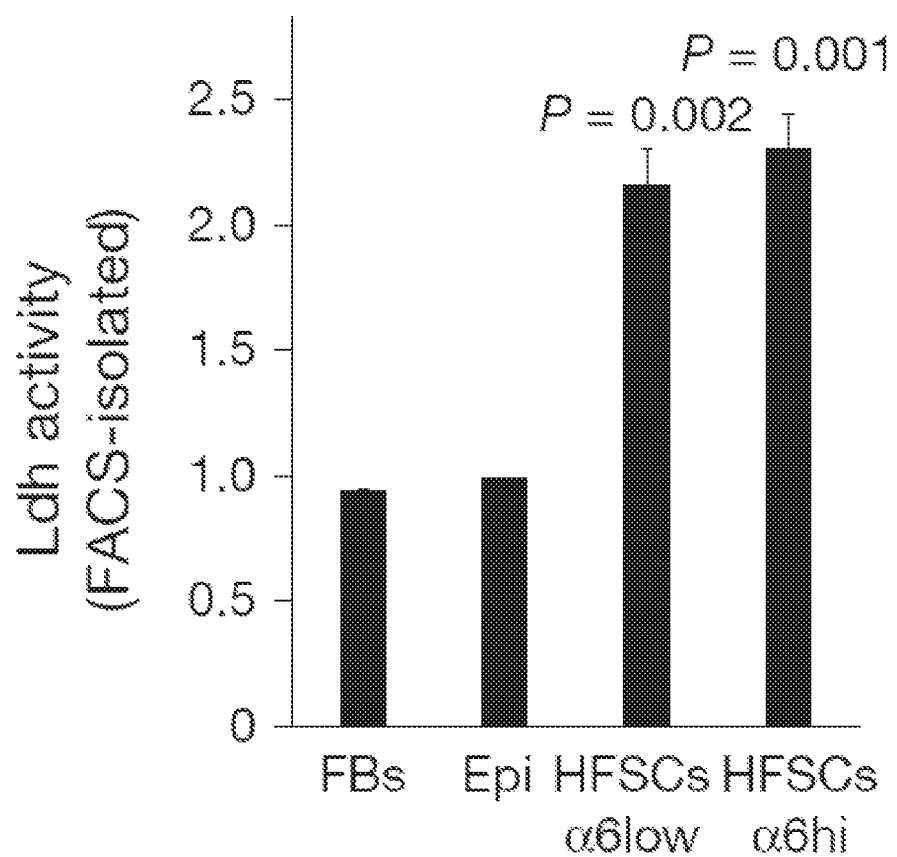
FIG. 1d, Ldh activity in sorted cell populations, measured using a plate reader-based assay, also shows the highest Ldh activity in two separate HFSC populations (α6low/Cd34$^+$ and α6hi/Cd34$^+$) compared to epidermal cells (Epi) and fibroblasts (FBs). Each bar represents the average signal for each cell type where n=9 mice pooled from 3 independent experiments. Shown as mean±s.e.m. Paired t-test performed. $P<0.05$ shown for each cell type versus epidermal cells.
Figure 1E:
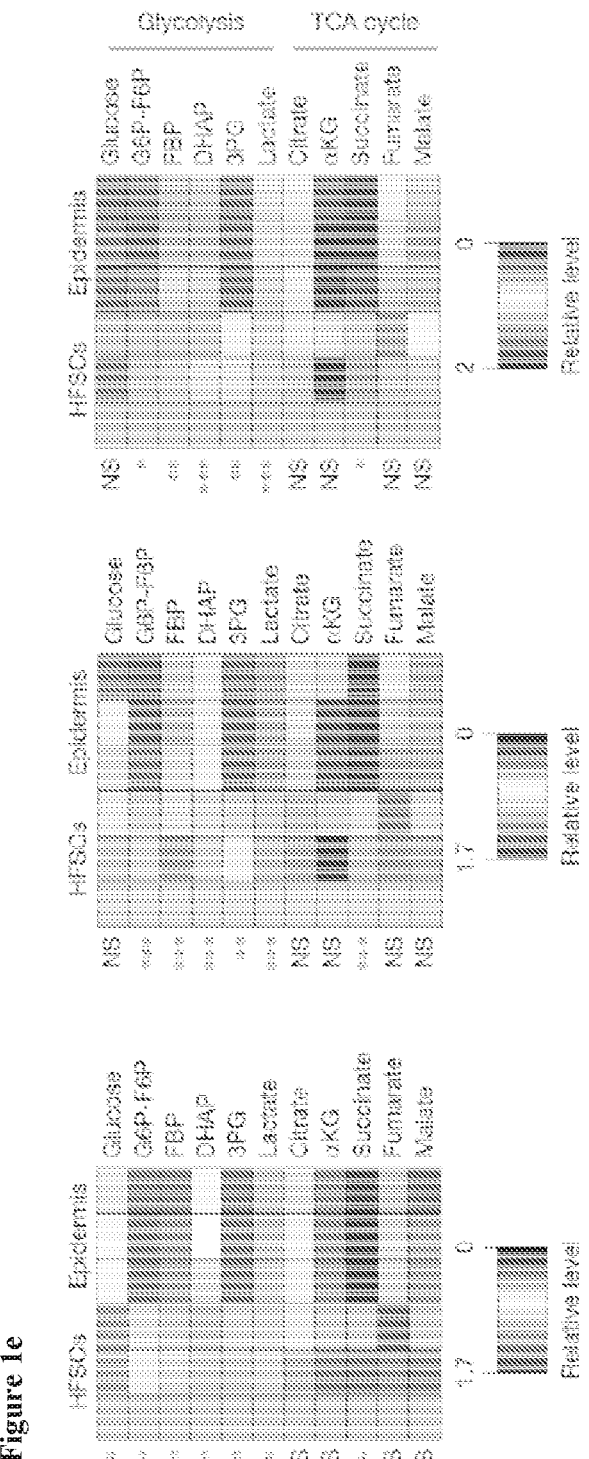
FIG. 1e, HFSCs and epidermal cells were isolated during telogen (day 50) by FACS, and metabolites were extracted and analyzed by LC-MS. Heatmaps show relative levels of glycolytic and TCA cycle metabolites from cells isolated from different mice in independent experiments with cells from three animals in each. G6P-F6P, glucose-6-phosphate and fructose-6-phosphate; FBP, fructose-bisphosphate; DHAP, dihydroxyacetone phosphate; 3PG, 3-phosphoglycerate; and αKG, alphaketoglutarate. Asterisks indicate significant difference in metabolite levels between epidermal cells and HFSCs.
Figure 4C:
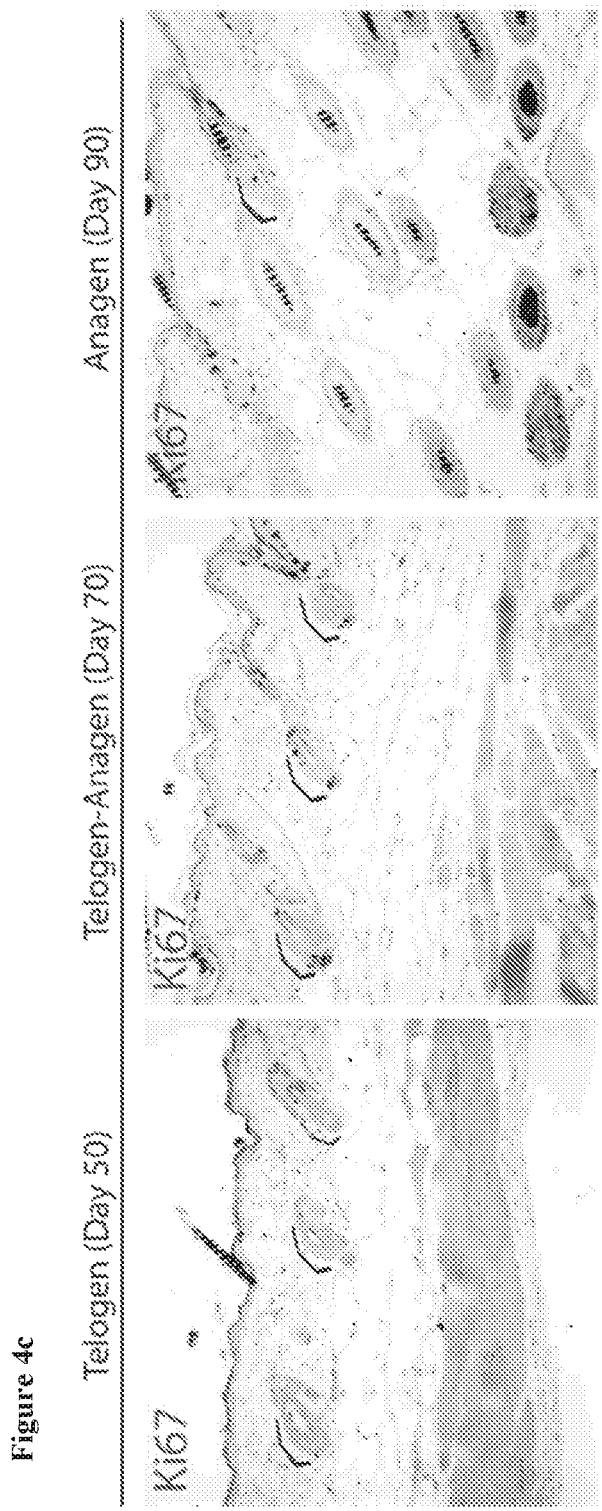
FIG. 4c. Staining for Ki-67 marks dividing cells during various stages of the hair cycle. Brackets indicate the HFSC niche.
Figure 4D:
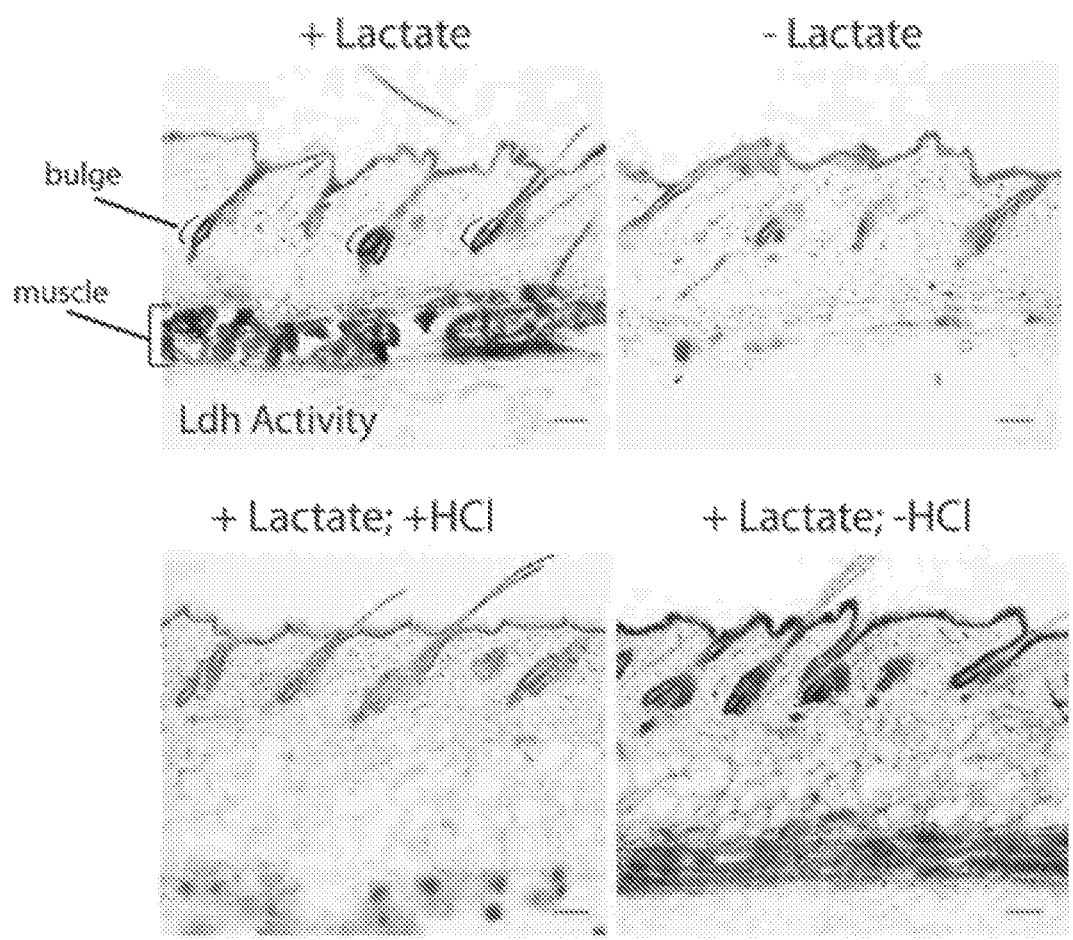
FIG. 4d, top, Validation of colorimetric Ldh enzyme activity assay. The highest Ldh enzyme activity was observed in HFSC bulge and in the muscle. Activity indicated by dark color, gray is nuclear fast red counterstain. In absence of substrate lactate there was no detectable activity (dark color). Bottom, Additional validation of colorimetric Ldh enzyme activity assay. Enzyme activity inhibited by treating skin with hydrochloric acid (HCl) before addition of staining solution with substrate lactate. No Ldh activity (dark color) detected. Skin in which enzyme activity is not inhibited by HCl shows highest Ldh enzyme activity in HFSC bulge and in the muscle. Scale bars, 50 µm.

Applying this assay to skin samples demonstrated that Ldh activity capacity was significantly higher in HFSCs, consistent with the expression pattern of Ldha (FIG. 1c). Furthermore, Ldh activity was enriched in HFSCs across the hair cycle (FIG. 1c). As a control, assays conducted without the enzymatic substrate (lactate) or on acid treated tissue yielded zero activity (FIG. 4d). To further validate these results, epidermal populations were sorted, cell lysates on the sorted cells were generated, and a similar colorimetric-based enzymatic assay was performed on the sorted cell lysates, which also showed increased Ldh activity in HFSCs (FIG. 1d). To better characterize the metabolism of HFSCs metabolomics analysis was performed on sorted populations from mouse skin by liquid chromatography-mass spectrometry (LC-MS) (FIG. 1e). Several glycolytic metabolites, including glucose/fructose-6-phosphate, fructose-bisphosphate, dihydroxyacetone phosphate, 3-phosphoglycerate, and lactate, were routinely higher in HFSCs relative to total epidermis across three independent experiments (isolated from different mice on different days). Conversely, most TCA cycle metabolites were not consistently different between the epidermis and HFSCs (FIG. 1e). Collectively these results suggest that while all cells in the epidermis use the TCA cycle extensively to generate energy, HFSCs also have increased Ldha expression, Ldh activity, and glycolytic metabolism.

Figure 4E:
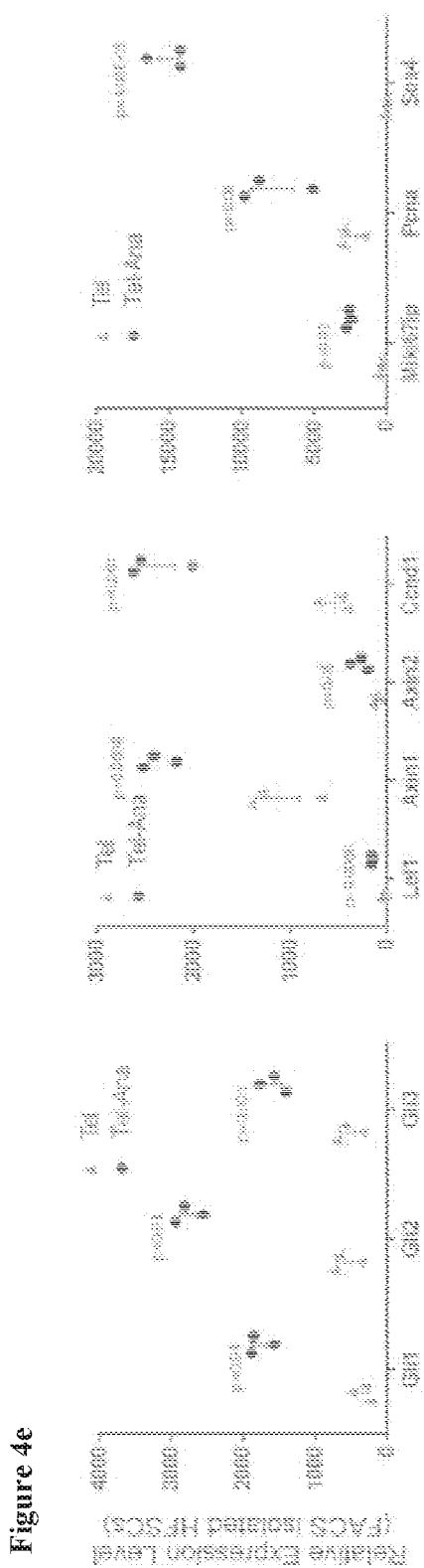
FIG. 4e, analysis of RNA-seq data to validate that HFSCs in telogen-anagen transition were in fact in such a transition. The telogen-anagen transition is known to be driven by Shh (Gli factors are targets) and Wnt (Lef1, Axin, Ccnd1 are targets) signaling, and correlate with increased proliferation (Ki67 and Pcna). In addition, Sox4 was previously identified as a regulator of the telogen-anagen transition.

Measuring metabolism across the hair cycle therefore would capture any dynamic changes that occur in HFSCs that correlate with activation or quiescence. Analysis of RNA-seq data from HFSCs isolated during either telogen or the telogen-anagen transition demonstrated not only that Ldha is the predominant Ldh isoform expressed in HFSCs (FIG. 1k), but is also induced during the telogen-anagen transition (FIGS. 1i and 1j) (NIHGEOGSE67404 and GSE51635). To confirm that the cells analyzed by RNA-seq were indeed either in telogen or the telogen to anagen transition, important markers of this transition were assessed including the Shh and Wnt pathways (Gli1, 2, 3: Lef1, Axin1, Axin2, Ccnd1) as well as proliferation markers (Ki-67. Pcna and Sox4) (FIG. 4e).

Figure 1F:
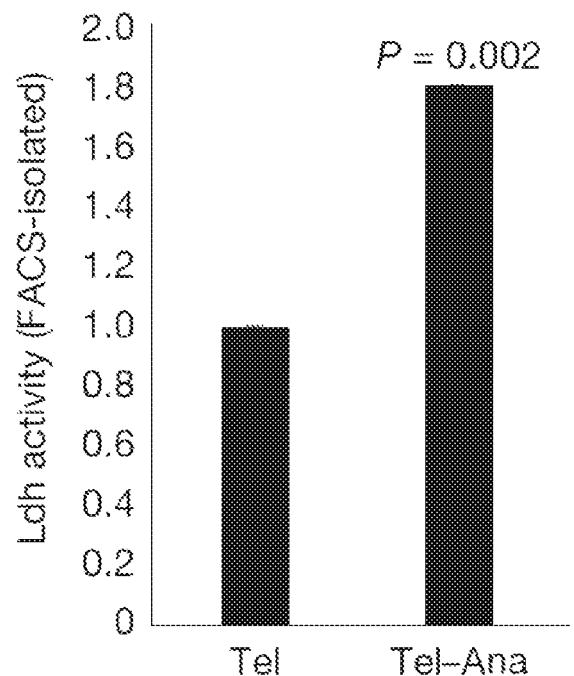
FIG. 1f, Ldh activity in sorted stem cell populations, measured using a plate reader-based assay, shows elevated Ldh activity as stem cells become activated in telogen to anagen transition (Tel-Ana).
Figure 1G:
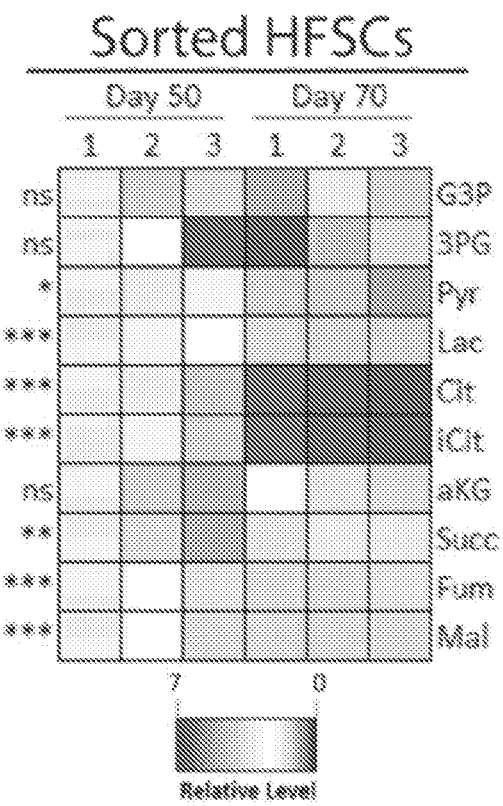
FIG. 1g, Heatmap showing relative levels of glycolytic and TCA cycle metabolites extracted from quiescent (Day 50) and activated (Day 70) HFSCs. Asterisks indicate significant difference between HFSCs metabolite levels.
Figure 1H:
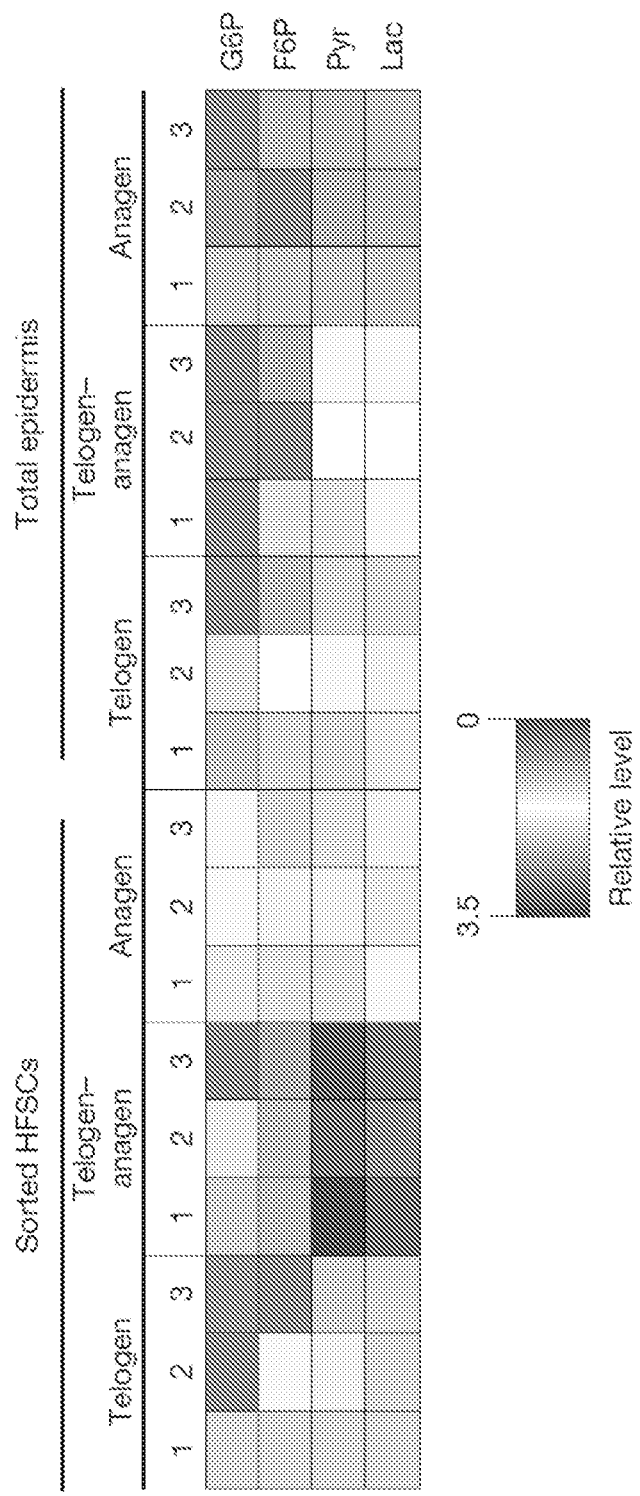
FIG. 1h, Heatmap showing relative levels of glycolytic and TCA cycle metabolites extracted from quiescent (telogen, day 50), activated (telogen-anagen, day 70) and HFSCs that have returned to the quiescent state (anagen, day 90). Pyr, pyruvate; Lac, lactate.
Figure 1I:
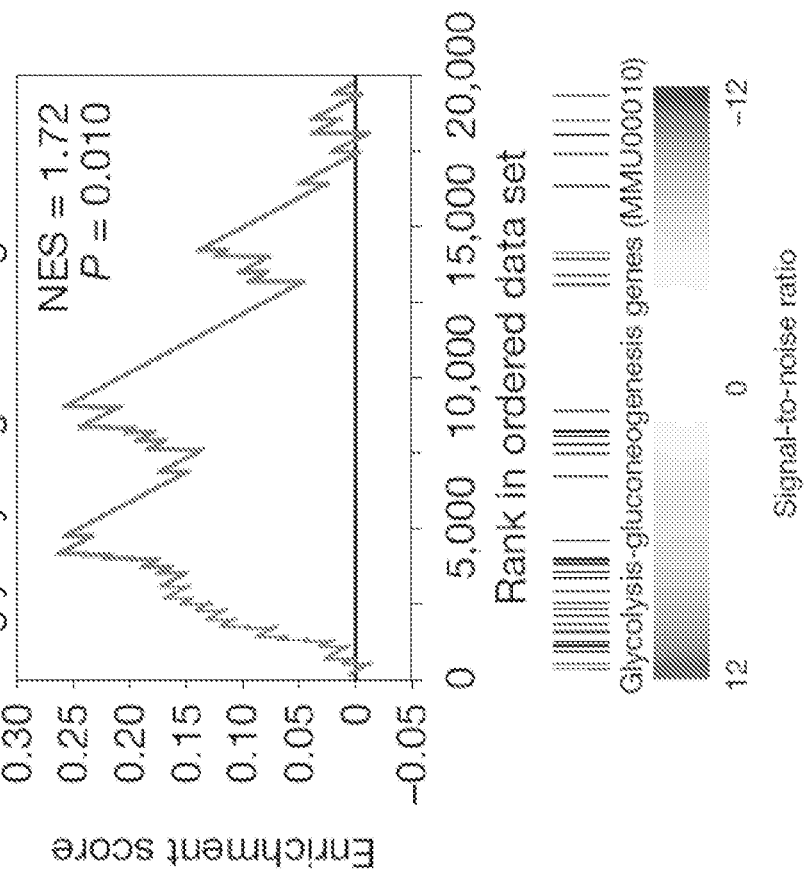
FIG. 1i, Gene set enrichment analysis (GSEA) from RNA-seq transcriptome data[11] from HFSCs versus total epidermis shows enrichment for glycolysis-related genes in HFSCs (normalized enrichment score (NES)=1.72)
Figure 1J:
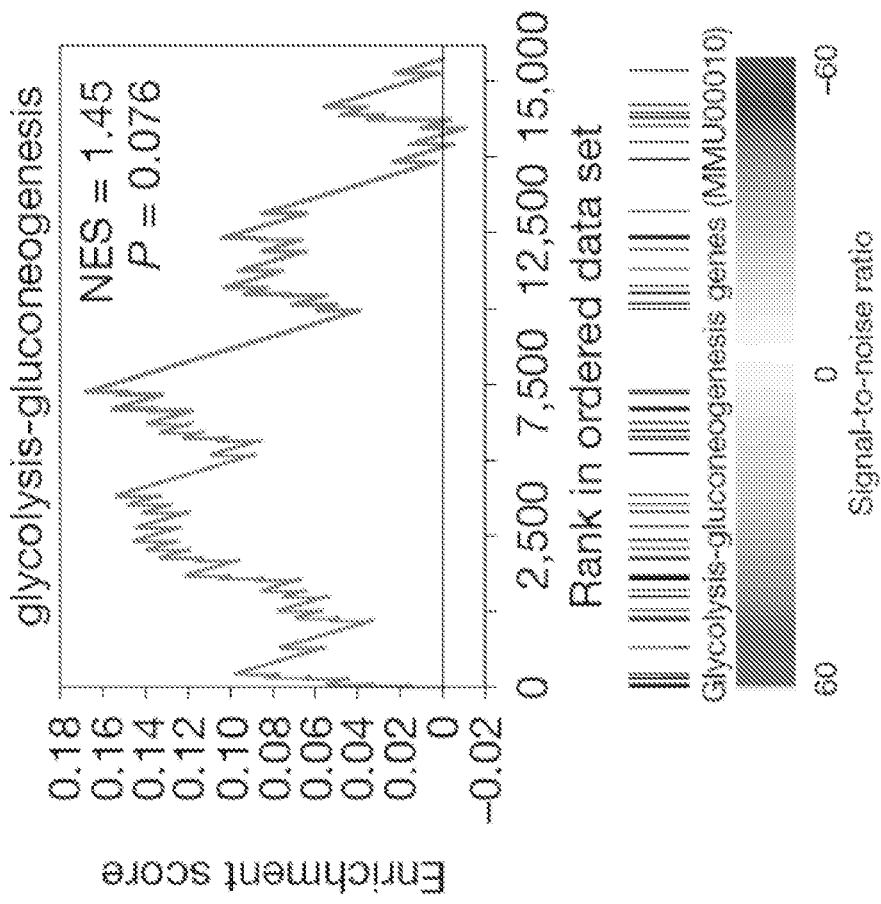
FIG. 1j, GSEA on microarray transcriptome data from HFSCs versus total epidermis shows enrichment for glycolysis-related genes in HFSCs (NES=1.45)
Figure 1K:
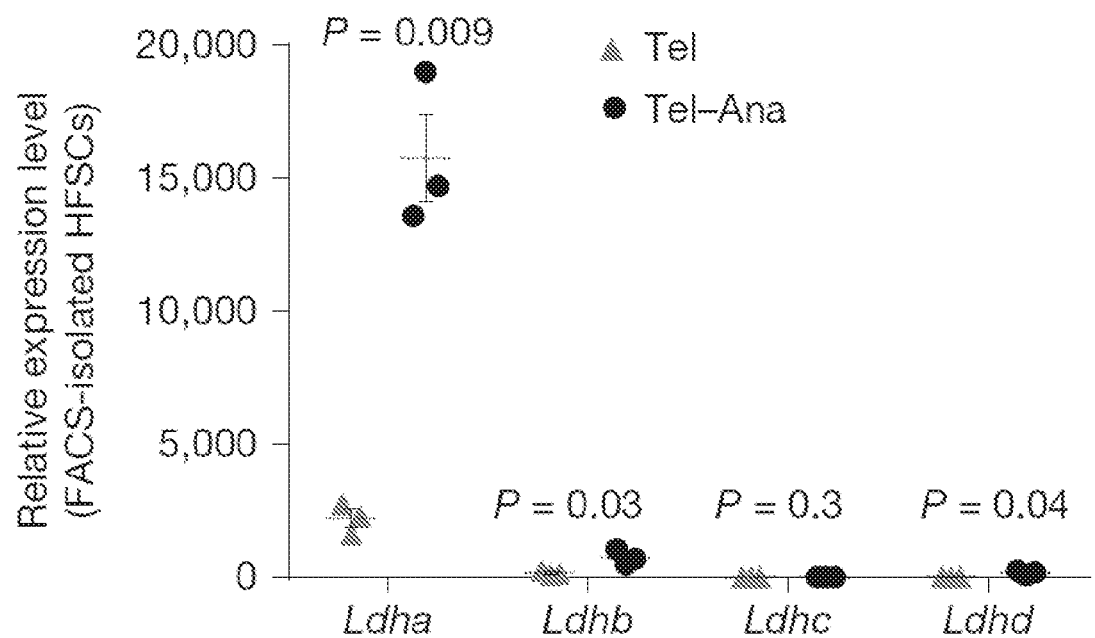
FIG. 1k, RNA-seq data from HFSCs sorted during telogen or telogen-anagen transition (Tel-Ana) show induction of Ldha.

The in vitro Ldh activity assay on lysates from sorted HFSCs uncovered a modest induction of Ldh activity correlating with the telogen to anagen transition (FIG. 1f, right). Hair cycle staging was validated by Ki-67 immunostaining to determine HFSC activation (FIG. 4c). Additionally, measurements of steady-state metabolites extracted from sorted HFSCs showed an increase in lactate in HFSCs as they transition from telogen to telogen-anagen transition, and then decrease again in anagen as HFSCs return to quiescence (FIG. 1h).

Example 2: Deletion of Ldh Activity Blocks HFSC Activation

Figure 2A:
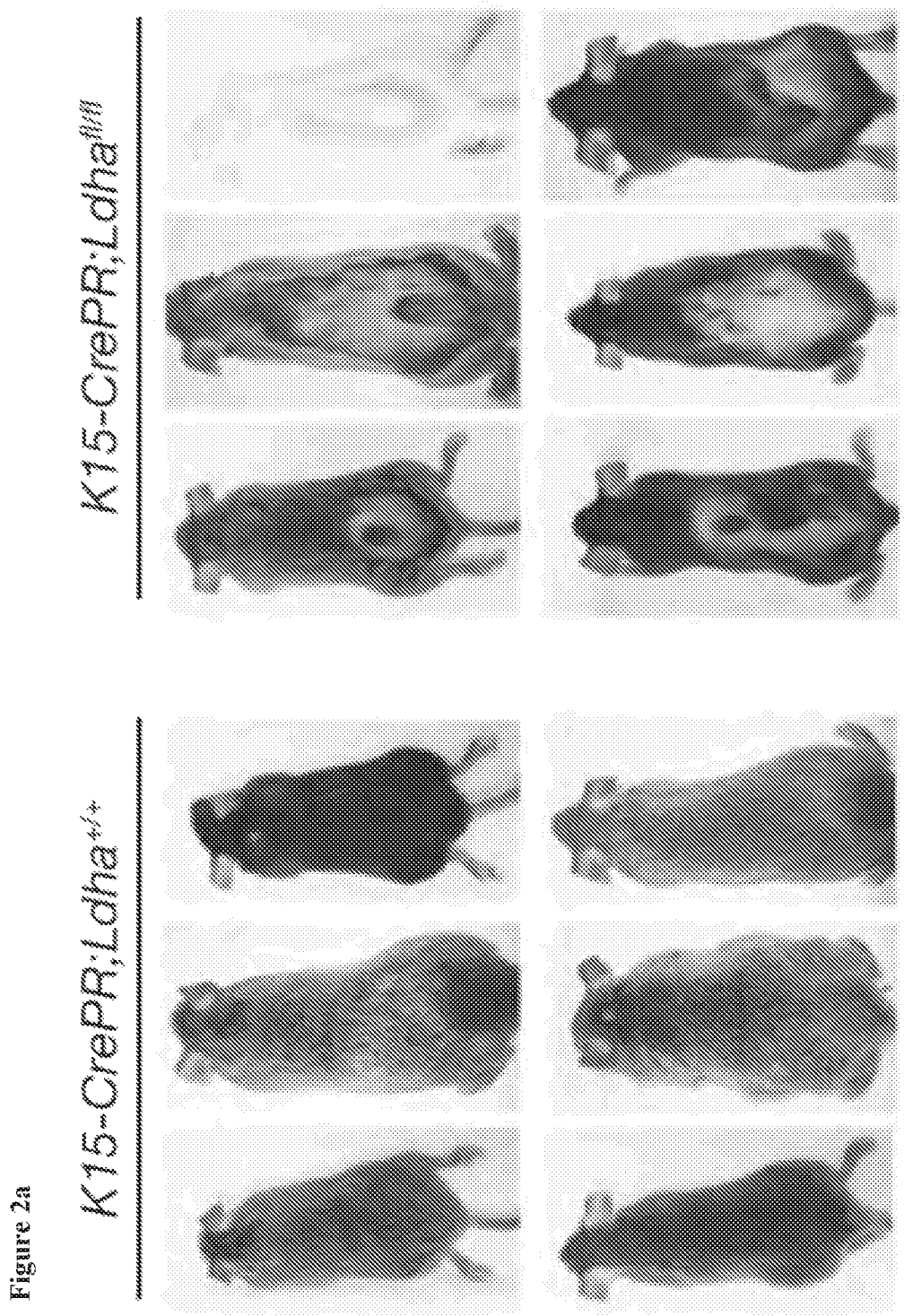
FIG. 2a shows deletion of Ldh activity blocked HFSC activation. Ldha$^{+/+}$ animals entered the hair cycle (anagen) synchronously around day 70 as measured by shaving and observation beginning at day 50. K15CrePR; Ldha$^{fl/fl}$ animals treated with mifeprisont show defects in anagen entry.

To determine whether Ldh activity is functionally related to the ability of HFSCs to remain quiescent or to activate at the start of a hair cycle, Ldha specifically was deleted in the HFSCs. Taking advantage of mice with floxed alleles of Ldha[12], this enzyme was deleted in HFSCs by crossing to mice bearing the K15CrePR allele[5], known to be inducible by Mifepristone specifically in HFSCs. Deletion of Ldha in HFSCs was initiated by administration of Mifepristone during telogen (day 50) and led to a typically mosaic recombination of the floxed alleles across the backskin. Mice with HFSC-specific deletion of Ldha failed to undergo a proper hair cycle, with most follicles remaining in telogen across at least 33 pairs of littermates 3-4 weeks after Mifepristone treatment (FIG. 2a).

Figure 2B:
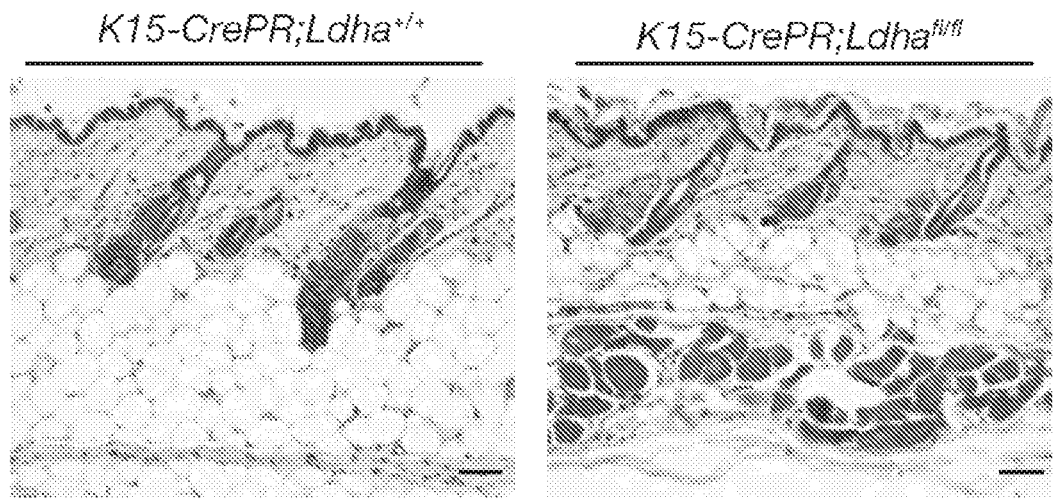
FIG. 2b, skin pathology showing that K15CrePR; Ldha$^{+/+}$ animals entered a normal anagen typified by downgrowth of the follicle and hypodermal thickening, while Ldha$^{fl/fl}$ animals showed neither and remained in telogen.
Figure 2C:
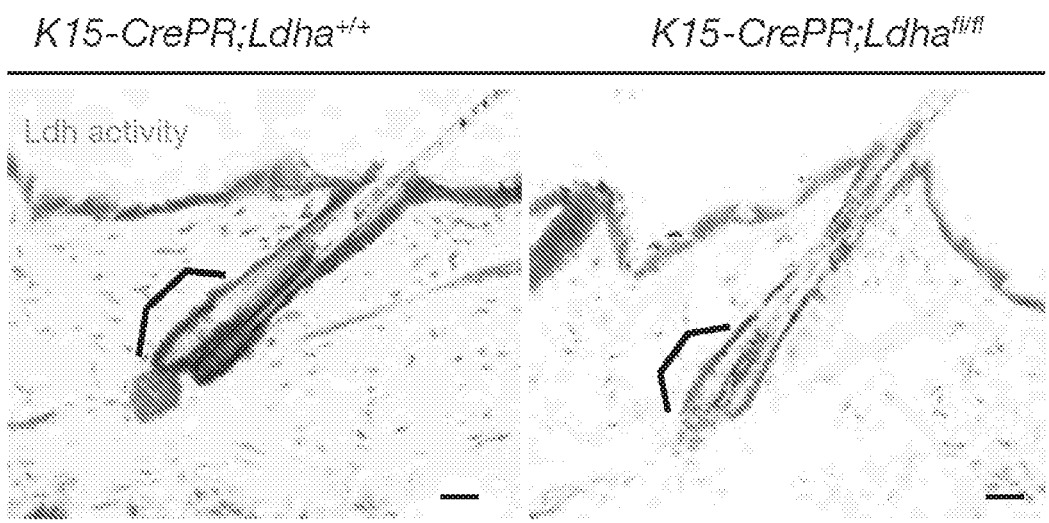
FIG. 2c, Ldh enzyme activity assay showed strong activity in HFSCs in K15CrePR; Ldha$^{+/+}$ animals, while K15CrePR; Ldha$^{fl/fl}$ animals lacked this activity in the HFSCs. (HFSC niche indicated by bracket).
Figure 2D:
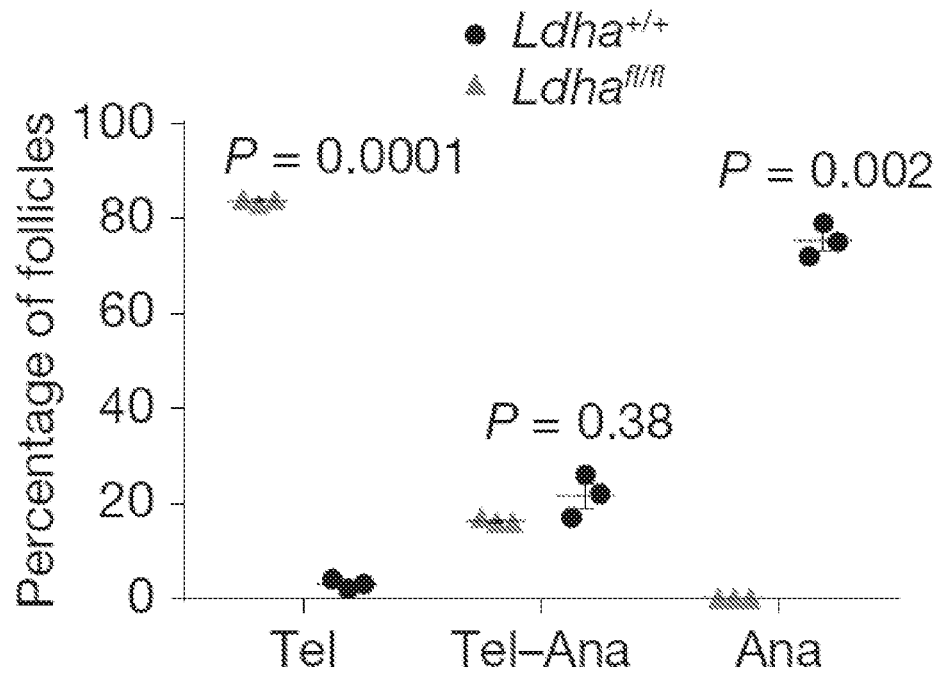
FIG. 2d, Graph showing percentage of follicles in telogen, telogen-anagen transition and anagen in K15CrePR; Ldha$^{+/+}$ mice versus K15CrePR; Ldha$^{fl/fl}$ mice.

Histology showed that WT hair follicles entered into the telogen to anagen transition typically by day 70, and this was accompanied by typical expansion of the hypodermis below (FIG. 2b). However, in backskin with deletion of Ldha, the hypodermis did not expand, and the telogen to anagen transition was severely abrogated (FIG. 2b). In areas of strong phenotypic penetrance, Ldh activity was severely abrogated in the HFSC compartment (FIG. 2c), demonstrating that the Ldha allele is critically important for Ldh activity in HFSCs and consistent with the fact that the 'a' isoform of Ldh is expressed at the highest level. Quantification of hair cycle progression across numerous animals indicated that most follicles lacking Ldha remained in telogen (FIG. 2d).

Figure 2E:
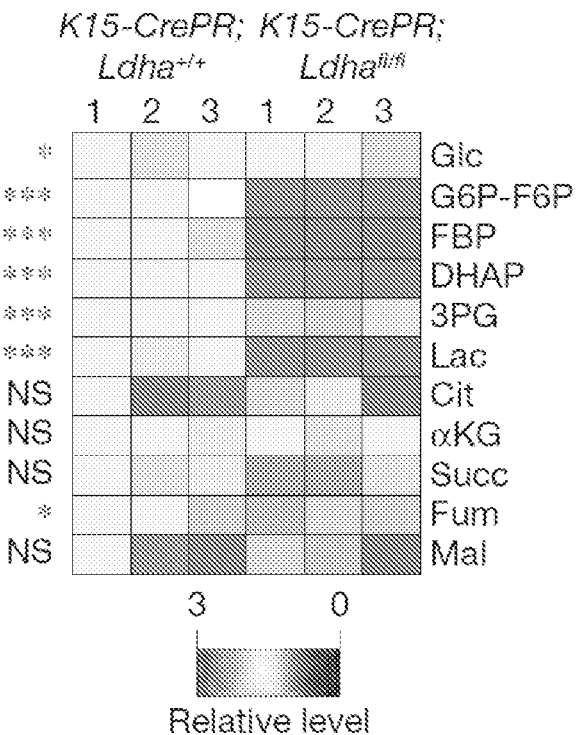
FIG. 2e, Heatmap showing relative levels of glycolytic and TCA cycle metabolites extracted from Ldha$^{+/+}$ HFSCs and Ldha$^{fl/fl}$ HFSCs and measured by LC-MS. Asterisks indicate significant difference between HFSCs metabolite levels.
Figure 2F:
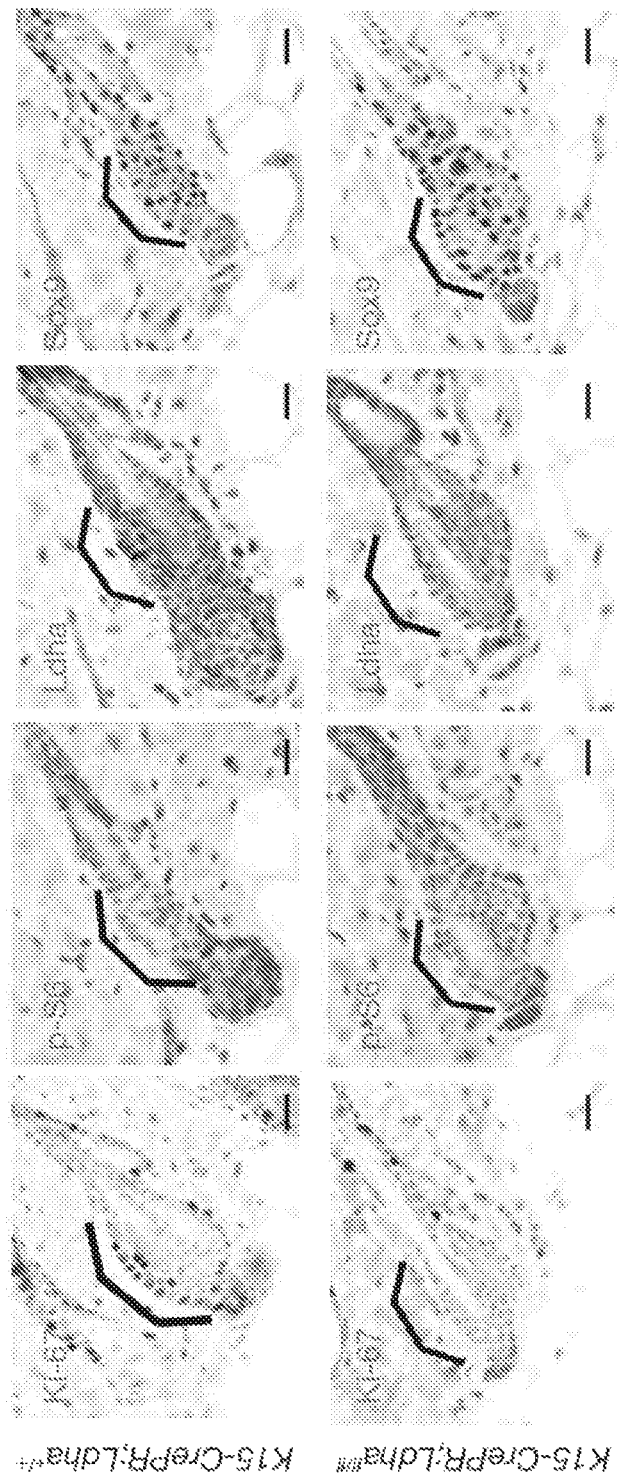
FIG. 2f, Immunohistochemistry staining for Ki-67, a marker of proliferation, is absent in Ldha$^{fl/fl}$ n HFSCs. Phospho-S6, a marker in HFSCs at the beginning of a new hair cycle, was absent in Ldha$^{fl/fl}$ HFSCs. Staining for Ldha showed specific deletion in HFSCs. Brackets indicate bulge. Staining for Sox9 shows that HFSCs were still present in Ldha-deleted niche. Scale bars, 20 µm.
Figure 2G:
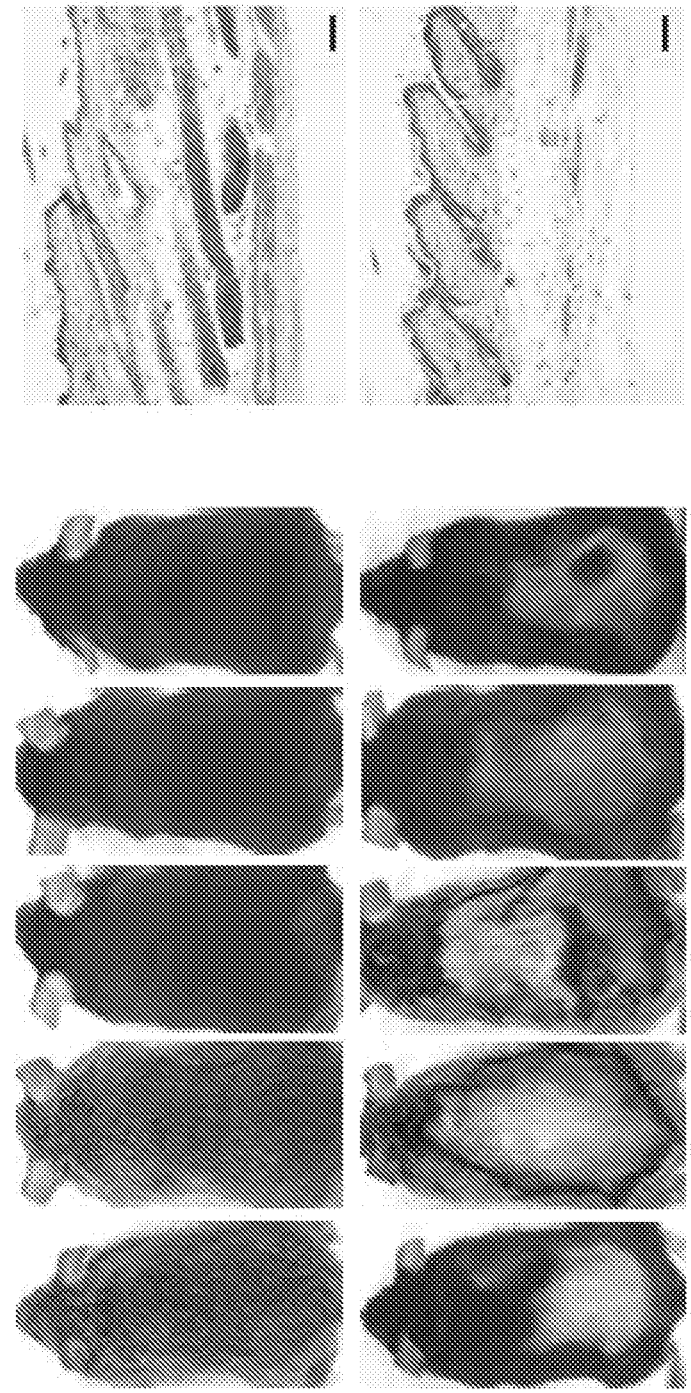
FIG. 2g, Animals which have Ldha deleted specifically in their HFSCs as controlled by Lgr5CreER, show profound defects in the entry into anagen. right, Skin pathology showing that Lgr5CreER;Ldha$^{fl/fl}$ animals mostly remained in telogen. Scale bars indicate 100 µm.
Figure 2H:
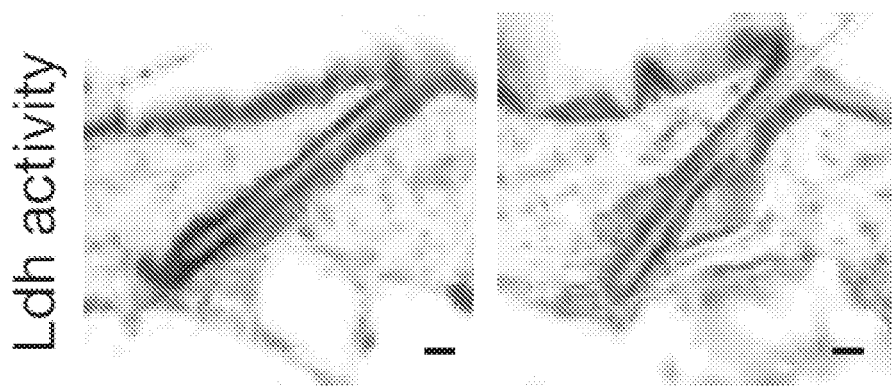
FIG. 2h, enzyme activity assay in the epidermis shows that Lgr5CreER;Ldha$^{fl/fl}$ animals lacked this activity in the HFSCs. Scale bars indicate 20 µm.
Figure 2I:
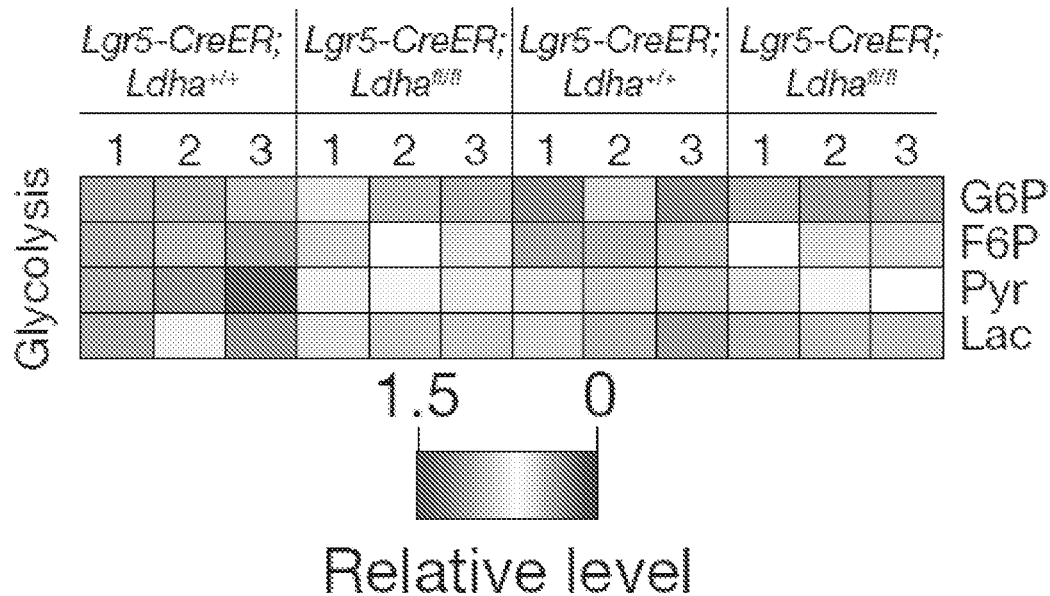
FIG. 2i, LC-MS analysis of metabolites from the indicated mice.

In addition, to confirm the phenotypes, Ldha also was deleted with an independent HFSC-specific Cre strategy. Lgr5-CreER has been used for lineage tracing in a variety of adult stem cell models, and has been shown to mark cells with high regenerative capacity, including HFSCs (Jaks, V. et al., Nat Genet 40, 1291-1299 (2008)). Lgr5CreER;Ldha$^{fl/fl}$ mice, treated with tamoxifen at post-natal day 50 prior to a synchronized hair cycle, also failed to activate anagen across at least 20 littermate pairs (FIG. 2g). In situ Ldh assay and metabolomics confirmed the successful deletion of Ldha in these animals (FIG. 2h and FIG. 2i).

Figure 4F:
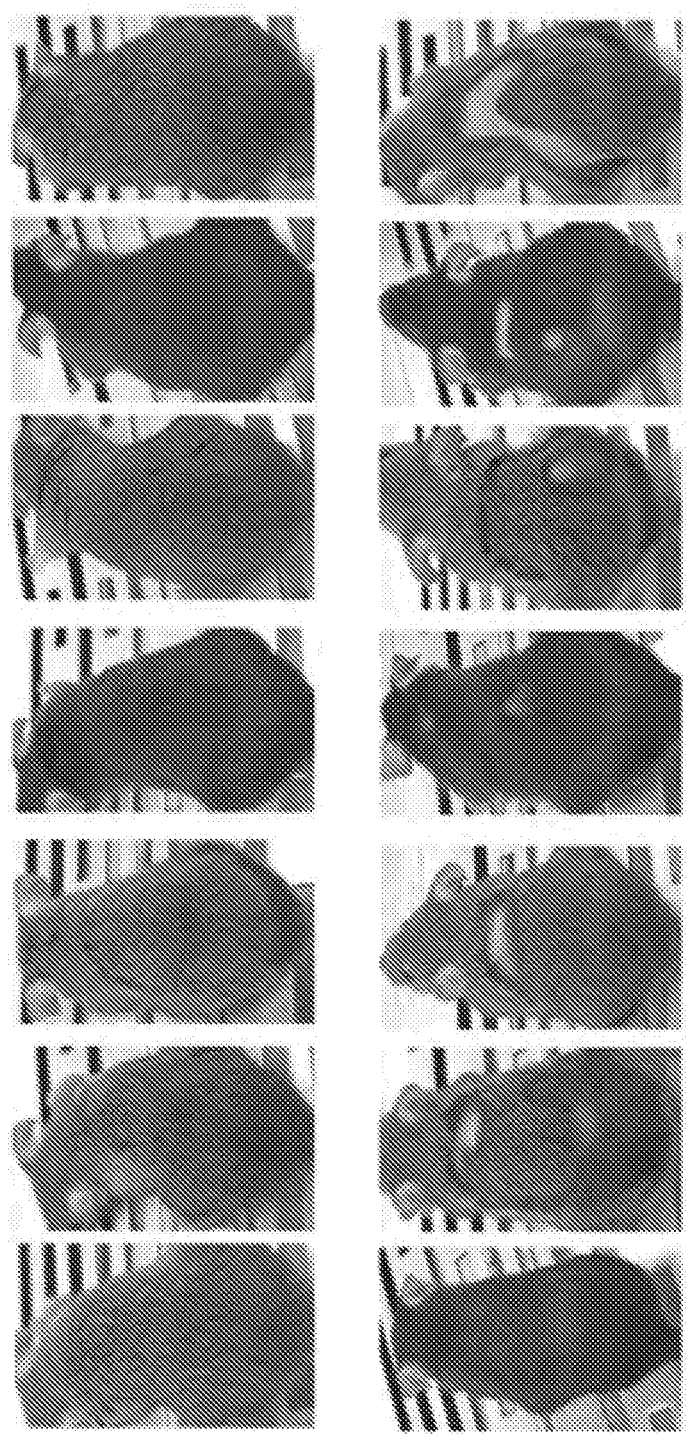
FIG. 4f, K15CrePR;Ldha$^{fl/fl}$ animals treated with Mifepristone during telogen (day 50) were allowed to develop for 6 months. None of the K15CrePR;Ldha$^{fl/fl}$ mice showed complete hair regrowth, compared to control animals that all grew their hair coats back completely.
Figure 4G:
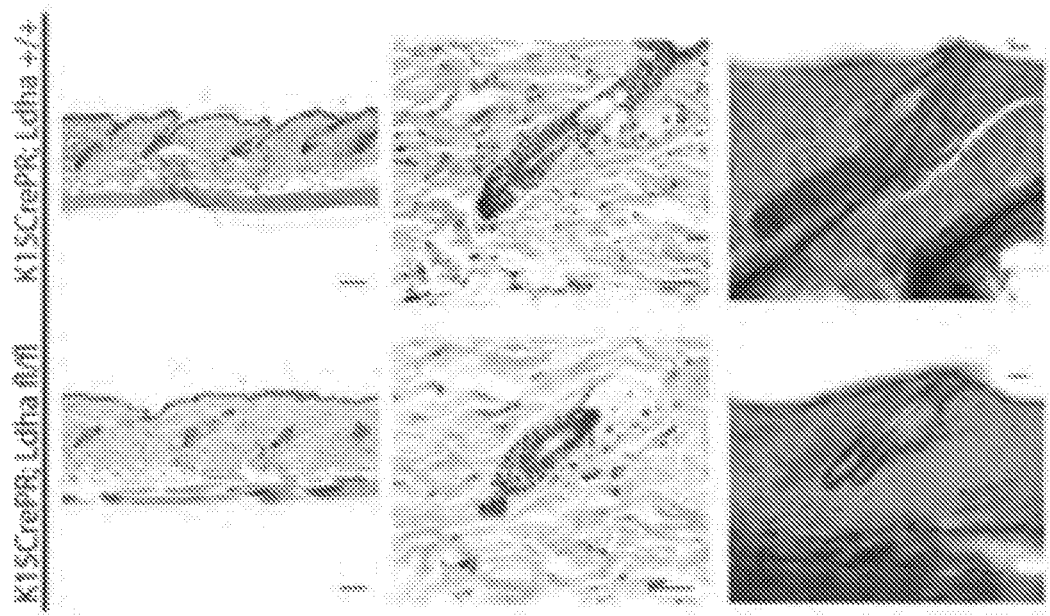
FIG. 4g, Histological examination of the long term K15CrePR;Ldha$^{fl/fl}$ mice showed that Ldha-null HFSCs remained in telogen while wild-type HFSCs went through anagen and then returned to telogen. This is apparent from thick sections (50 micron, right) that show an increased number of club hairs in the WT relative to Ldha-null follicles. Scale bars indicate 100 micrometers (left), and 20 micrometers (middle and right).
Figure 4H:
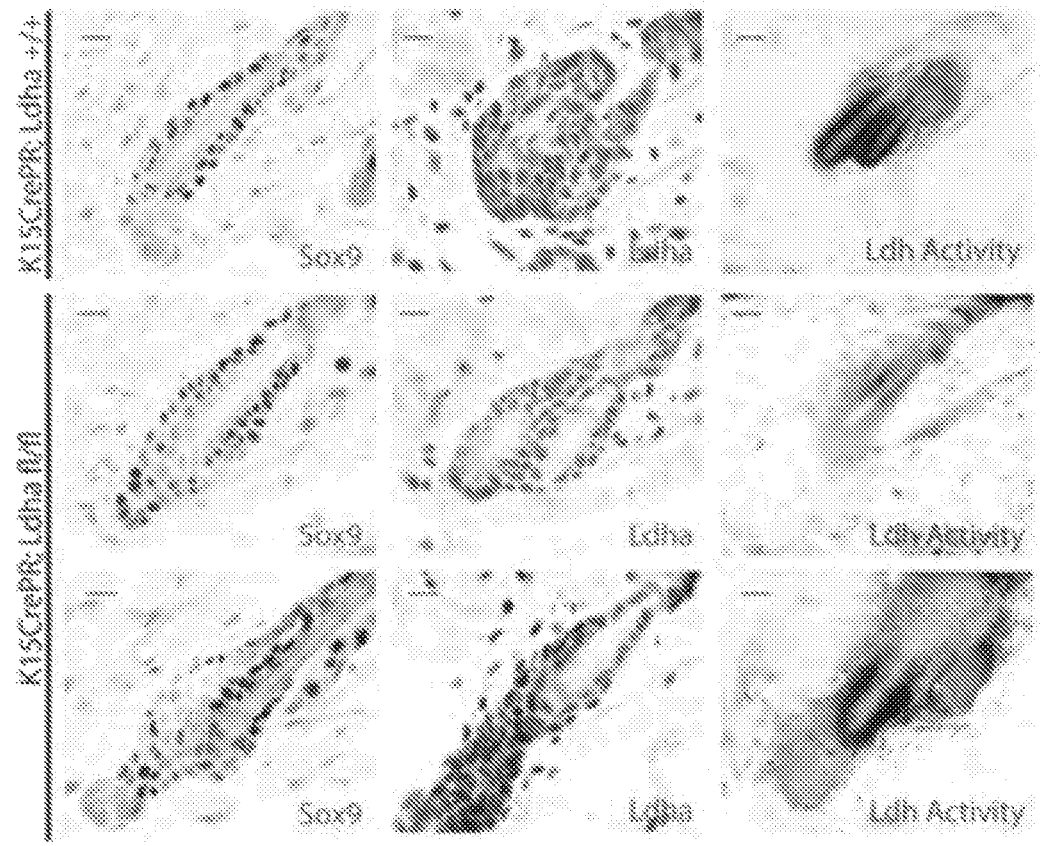
FIG. 4h, IHC for HFSC marker Sox9 showed that deletion of Ldha from HFSCs does not affect their presence in the bulge even after 6 months. In addition, IHC and Ldh activity assay demonstrate that the deletion of Ldha was sustained. Because of the mosaicism of the deletion, in some portions of K15CrePR;Ldha$^{fl/fl}$ skin Ldha was not deleted. Shown on the bottom row is tissue from hair bearing skin in the K15CrePR;Ldha$^{fl/fl}$ mice where Ldha was still expressed, showing that new hair growth in K15CrePR;Ldha$^{fl/fl}$ mice was due to lack of deletion of Ldha caused by the mosaic approach used to mediate Cre recombination. Scale bars indicate 20 micrometers.

The effect of loss of Ldha activity in K15+ cells was monitored over a six month period and found that deletion of Ldha led to a mosaic, but permanent block of HFSC activation in some portions of the backskin (FIG. 4f). These data confirm that Ldh activity is required for HFSC activation, and is not simply a marker of HFSCs. A closer look at these long term Ldha deletions showed that Ldha-null HFSCs continued expressing typical markers, but lacked Ldh activity, and failed to initiate new hair cycles, while those follicles that escaped deletion continued to express Ldha and to cycle normally (FIG. 4g and FIG. 4h).

Figure 3A:
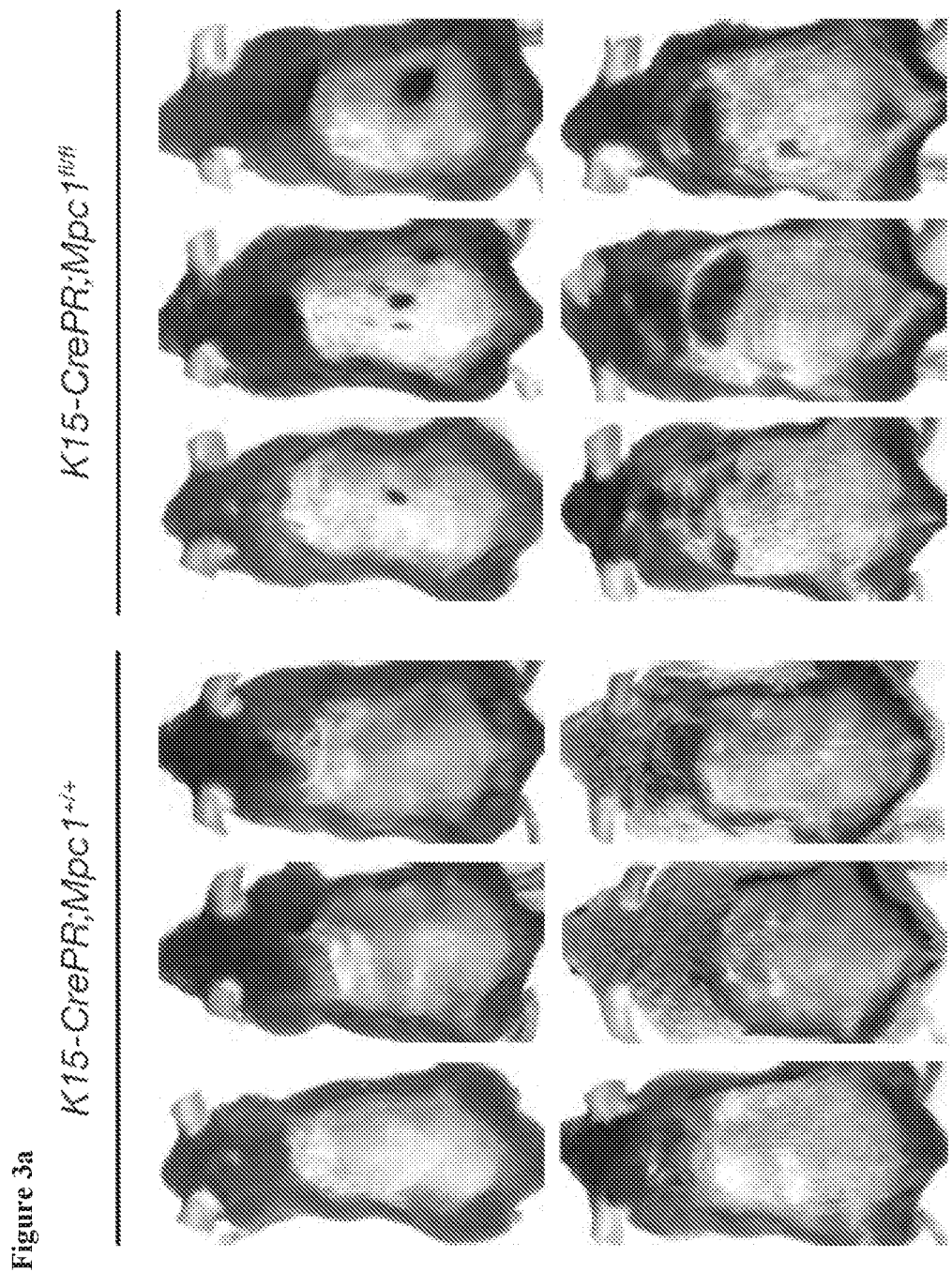
FIG. 3a shows deletion of Mpc1 in Hair Follicle Stem Cells activated a new hair cycle. Mpc1$^{fl/fl}$ animals showed pigmentation and hair growth, consistent with entry into the anagen cycle at 9 weeks, whereas Mpc1$^{+/+}$ animals did not show pigmentation and hair growth this early.
Figure 3B:
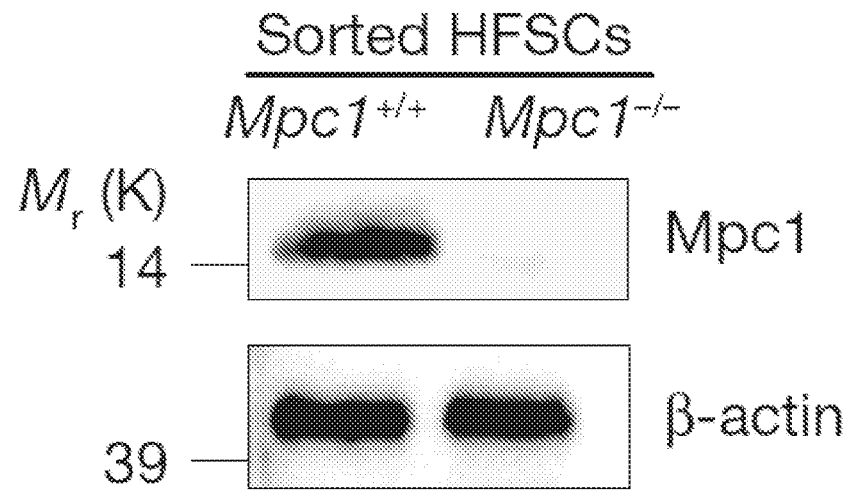
FIG. 3b, FACS isolation of HFSC bulge populations in Mpc1$^{+/+}$ versus Mpc1$^{fl/fl}$ mice followed by western blotting showed successful deletion of Mpc1 protein in the stem cell niche. β-actin is a loading control.
Figure 3C:
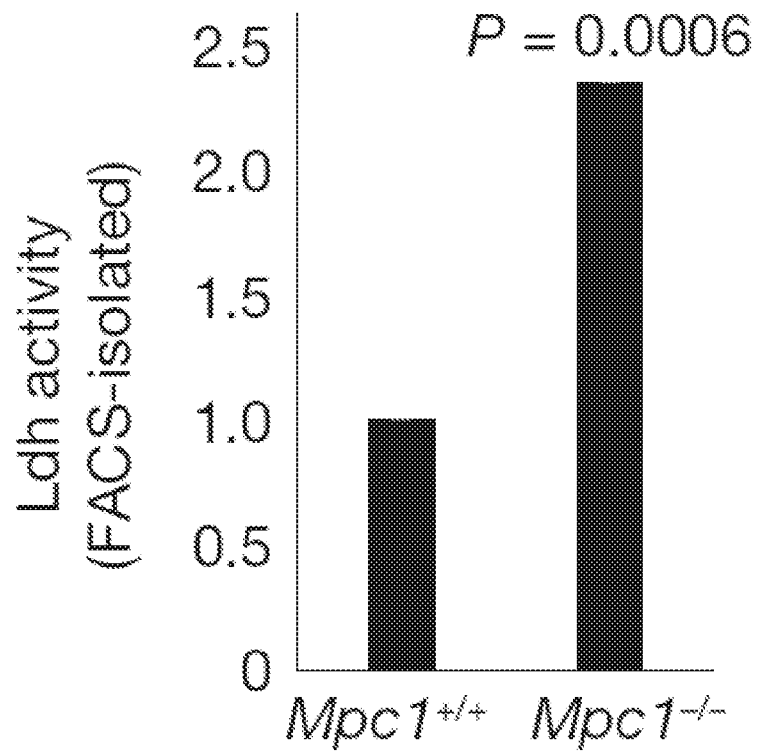
FIG. 3c, Platereader assay for Ldh activity on sorted HFSC populations shows elevated activity in Mpc1$^{fl/fl}$ HFSCs compared to Mpc1$^{+/+}$ HFSCs.
Figure 3D:
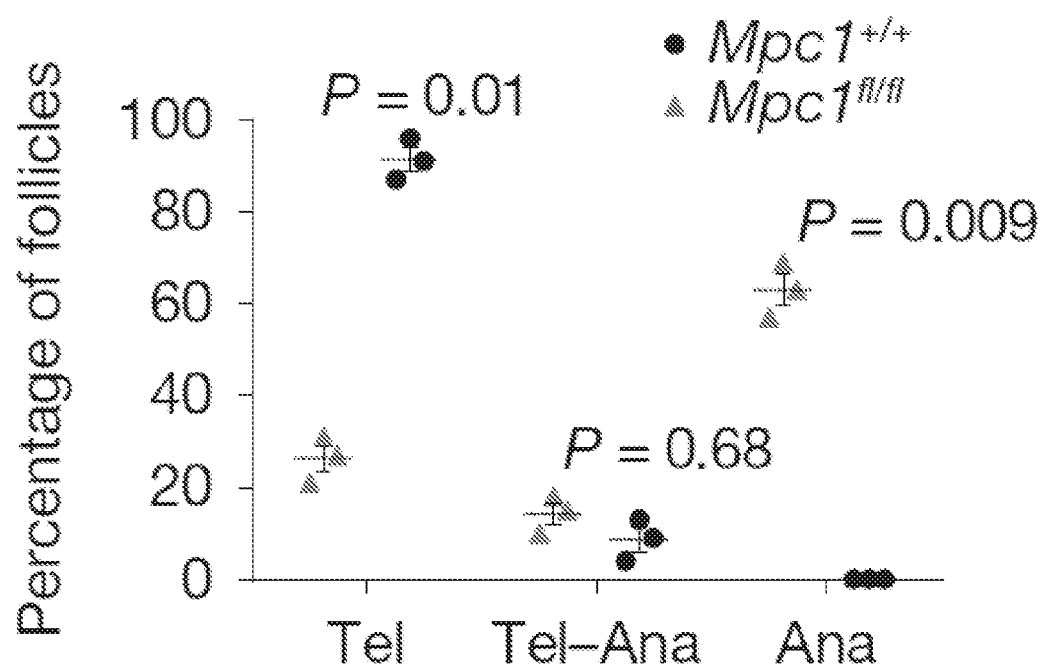
FIG. 3d. Quantification of phenotype at right shows percentage of follicles in telogen, telogen to anagen transition and anagen in Mpc1$^{+/+}$ mice versus Mpc1$^{fl/fl}$ mice.
Figure 3E:
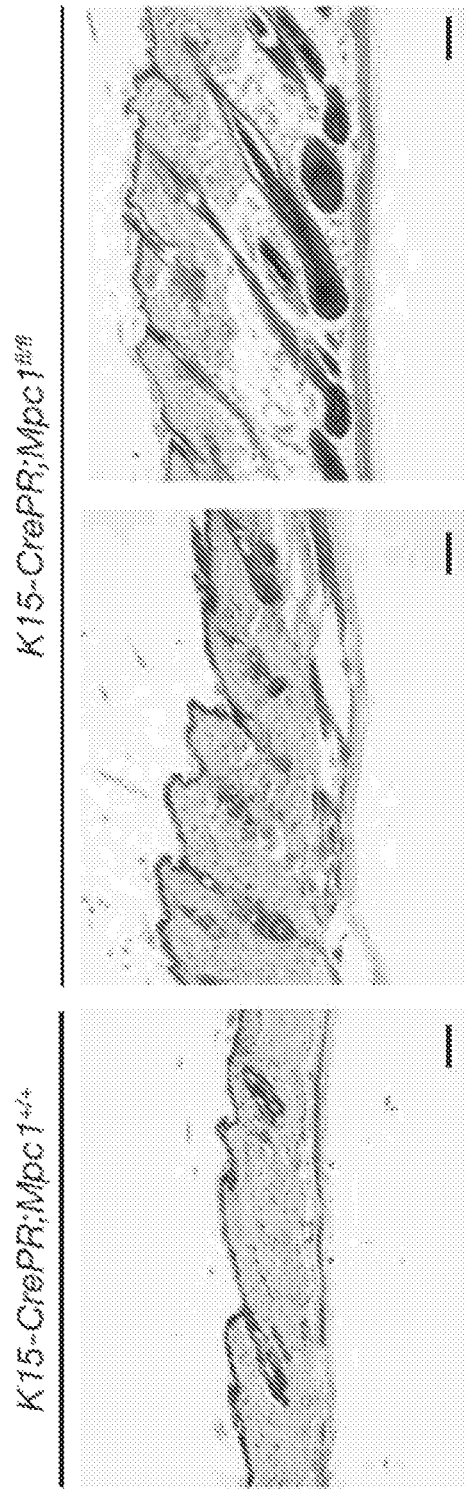
FIG. 3e, Histology on wild-type versus Mpc1 deletion skin showed induction of anagen in absence of Mpc1. Scale bars indicate 100 µm.
Figure 3F:
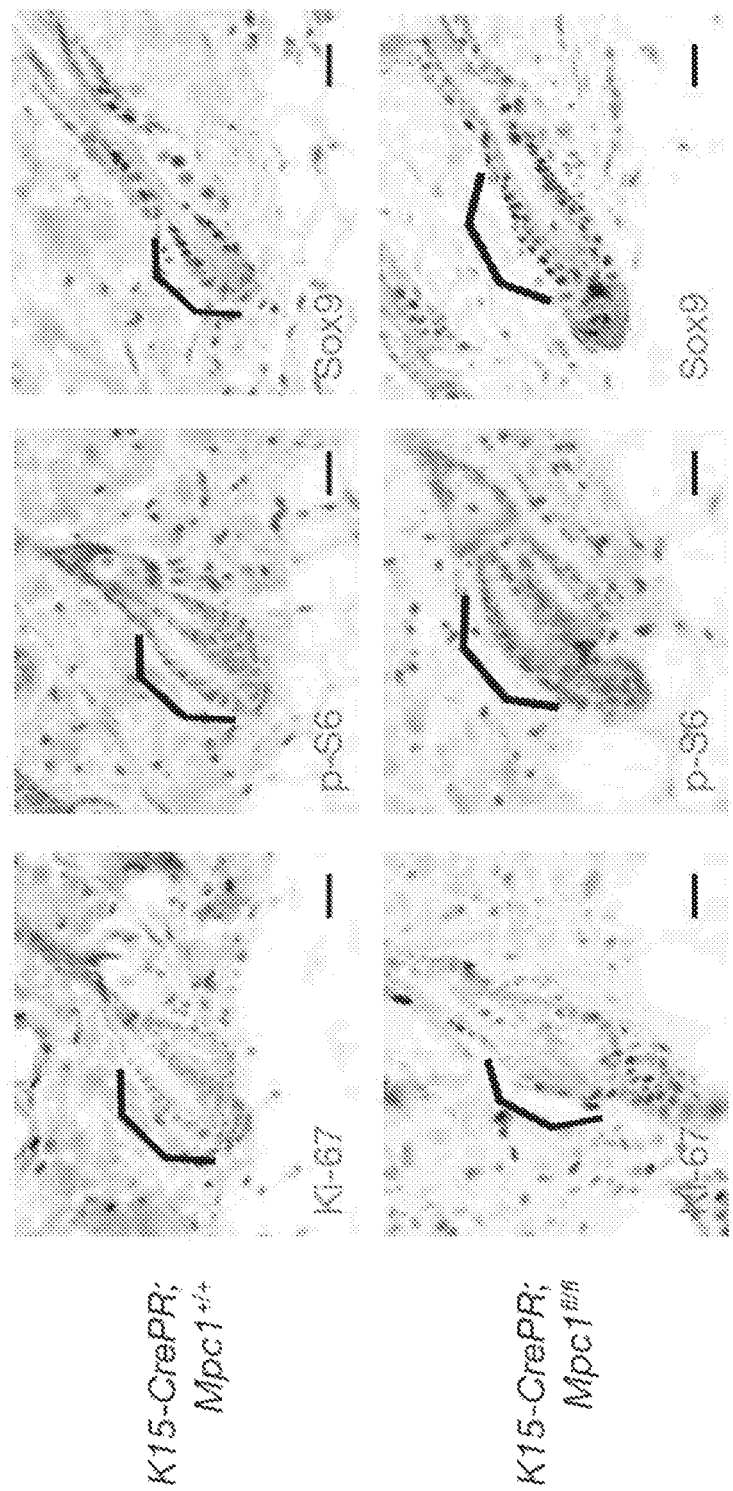
FIG. 3f, Immunohistochemistry staining for Ki-67, a marker of proliferation that is only active in HFSCs at the beginning of a new hair cycle, was only present in Mpc1$^{fl/fl}$ HFSCs at 8.5 weeks, consistent with their accelerated entry into a new hair cycle. Phospho-S6, another marker that is only active in HFSCs at the beginning of a new hair cycle, was only present Mpc1$^{fl/fl}$ HFSCs. Staining for Sox9 shows that HFSCs were present in Mpc1 deleted niche.
Figure 3G:
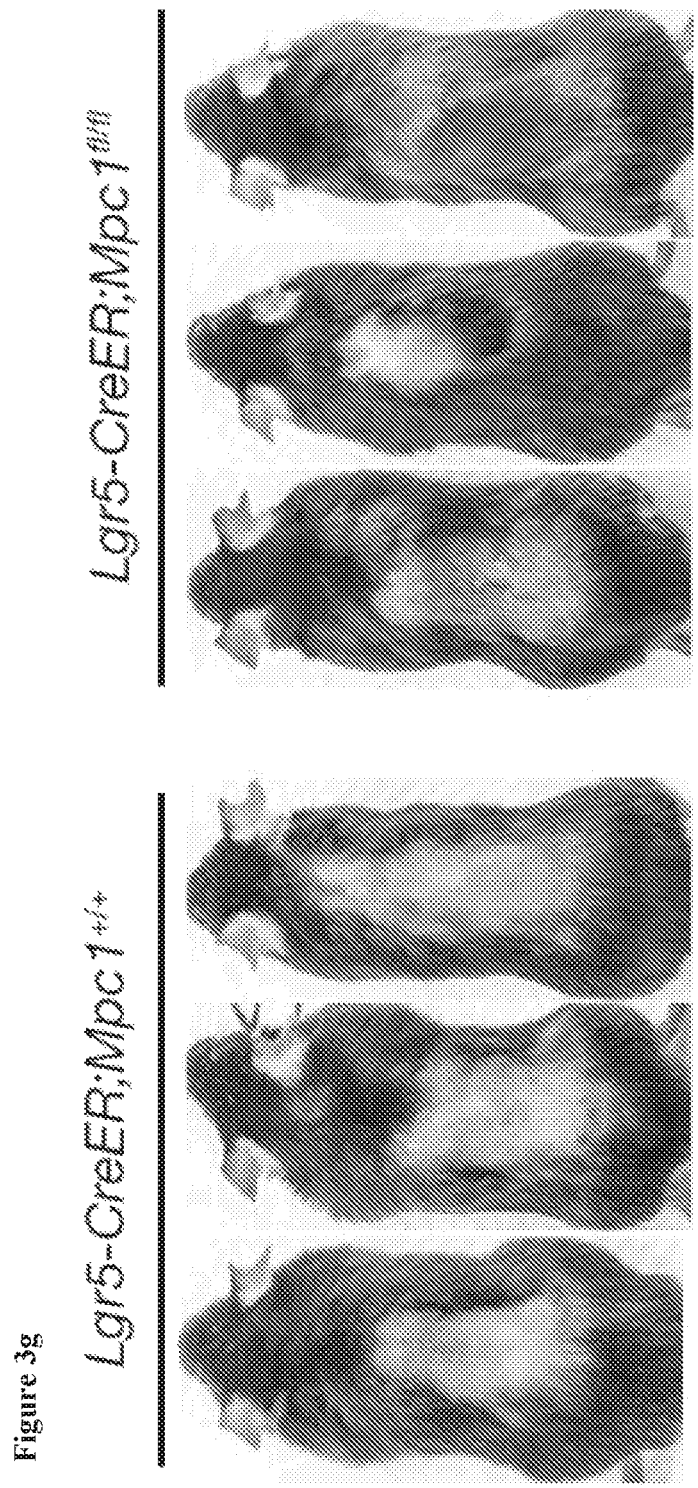
FIG. 3g, Deletion of Mpc1 in mice bearing the Lgr5CreER allele shows strong induction of the hair cycle. Note that red boxes indicate areas of new hair growth.
Figure 3H:
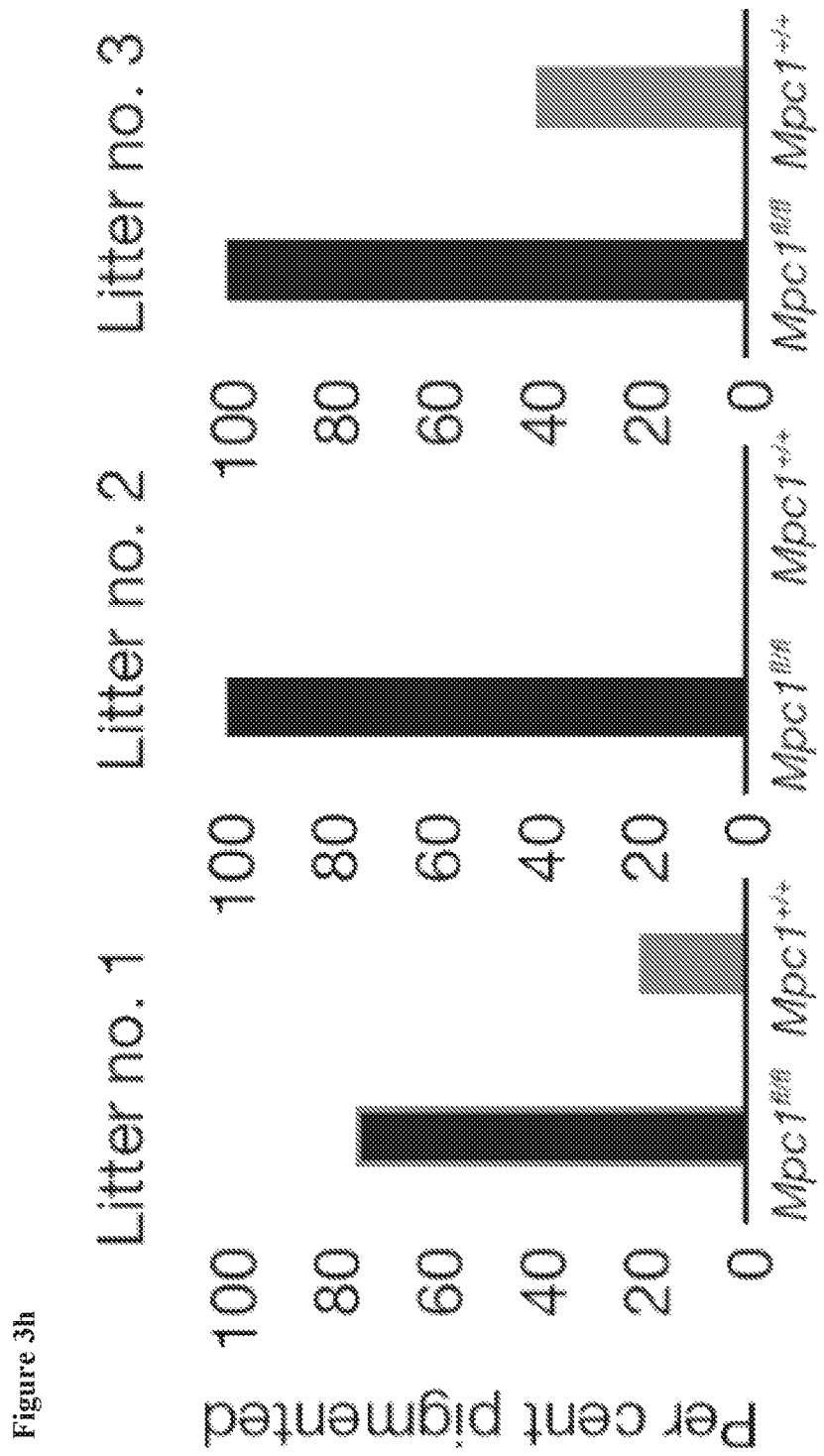
FIG. 3h, Quantification of pigmentation in the indicated genotypes across three independent litters.
Figure 4I:
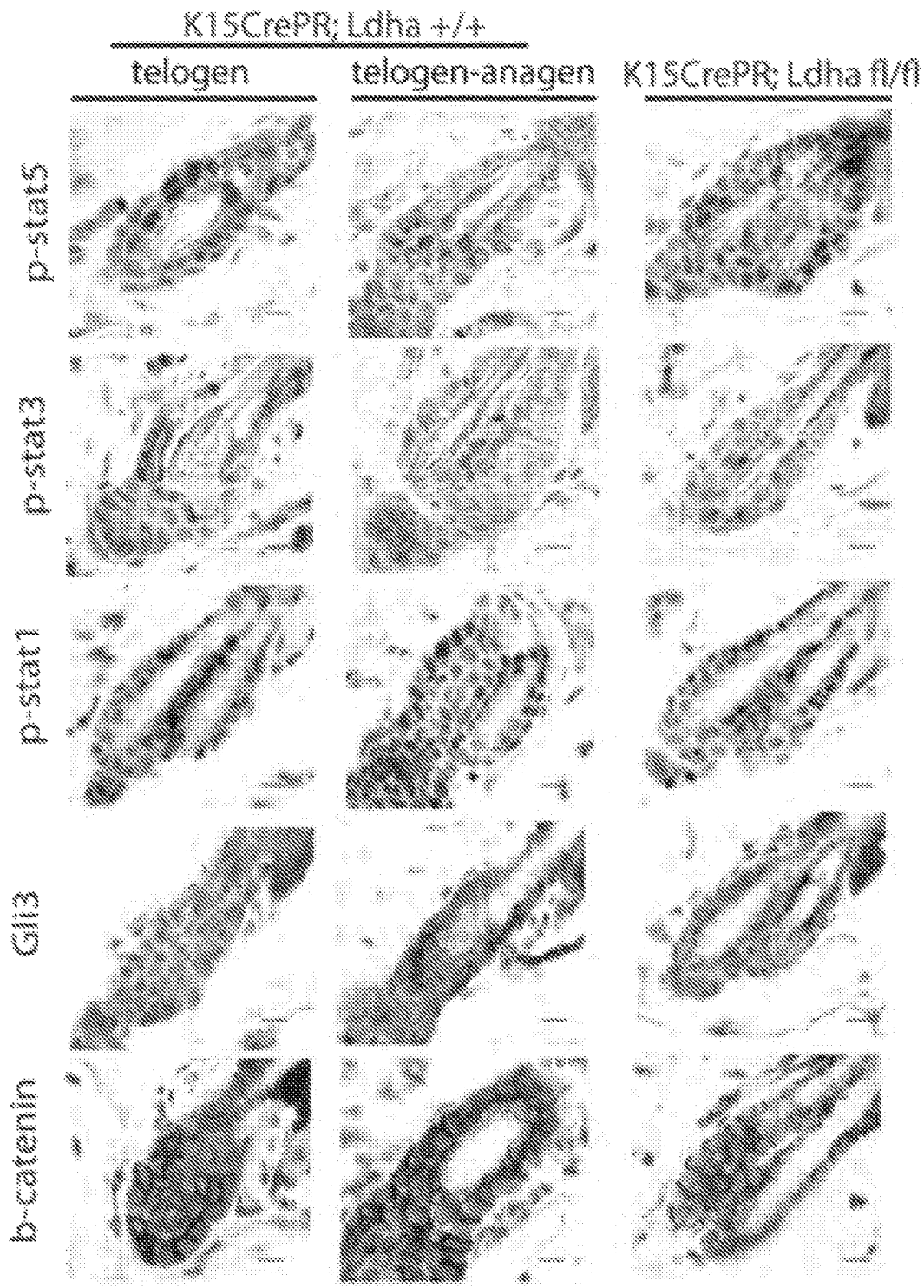
FIG. 4i, To determine how various signaling pathways previously linked to the hair cycle are affected by loss of Ldha in HFSCs, we performed IHC for markers that indicate activity of these pathways in telogen and telogen-anagen transition. Note that pStat5 appears to be suppressed in normal telogen-anagen transition, and this does not seem to occur in Ldha-null HFSCs. pStat1 and pStat3 did not seem to be affected by loss of Ldha. Expression of Gli3, a target of Shh signaling, is typically induced in an activated hair germ derived from HFSCs, but Ldha-null HFSCs do not make an active hair germ. Activation of the Wnt pathway is indicated by nuclear localization of β-catenin, and very little nuclear β-catenin was detected in Ldha-null HFSCs. Scale bars indicate 6 micrometers.

After sorting HFSCs from animals with or without Ldha deletion, LC-MS-based metabolomics analysis demonstrated that lactate levels, as well as levels of other glycolytic metabolites, were strongly reduced in the absence of Ldha (FIG. 2e), functional evidence that the targeting strategy was successful. The fact that glycolytic metabolites upstream of lactate were also suppressed suggests that HFSCs could be adapting their metabolism to account for the loss of Ldh activity. Immunostaining for markers of HFSC activation and proliferation indicated a failure of HFSC activation. Ki67 and pS6 have been clearly demonstrated to be abundant in the HFSC niche at the start of the hair cycle[13], and both of these markers were absent in Ldha deleted backskin (FIG. 3f). Immunostaining for Ldha also confirmed successful deletion of this protein, while staining for Sox9, a marker of HFSCs indicated that these cells remained in their niche, but just failed to activate in the absence of Ldha (FIG. 3f). Induction of the hair cycle is also thought to be regulated by signaling from the Shh, Wnt and Jak-Stat pathways. Each of these was assayed by IHC in normal or Ldha deletion follicles, and it was found that in general these pathways were not activated in Ldha-null HFSCs that failed to enter a telogen-anagen transition (FIG. 4i).

Example 3: Deletion of Mpc1 in Hair Follicle Stem Cells Activates a New Hair Cycle K15CrePR animals were crossed to those floxed for mitochondrial pyruvate carrier 1 (Mpc1) (K15CrePR; Mpc1$^{fl/fl}$). Mpc1, as a heterodimer with Mpc2, forms the mitochondrial pyruvate carrier MPC, a transporter on the inner mitochondrial membrane required for pyruvate entry into the mitochondria[15]. Loss of function of Mpc1 has been shown to drive lactate production through enhanced conversion of pyruvate to lactate by Ldh[16].

Figure 4J:
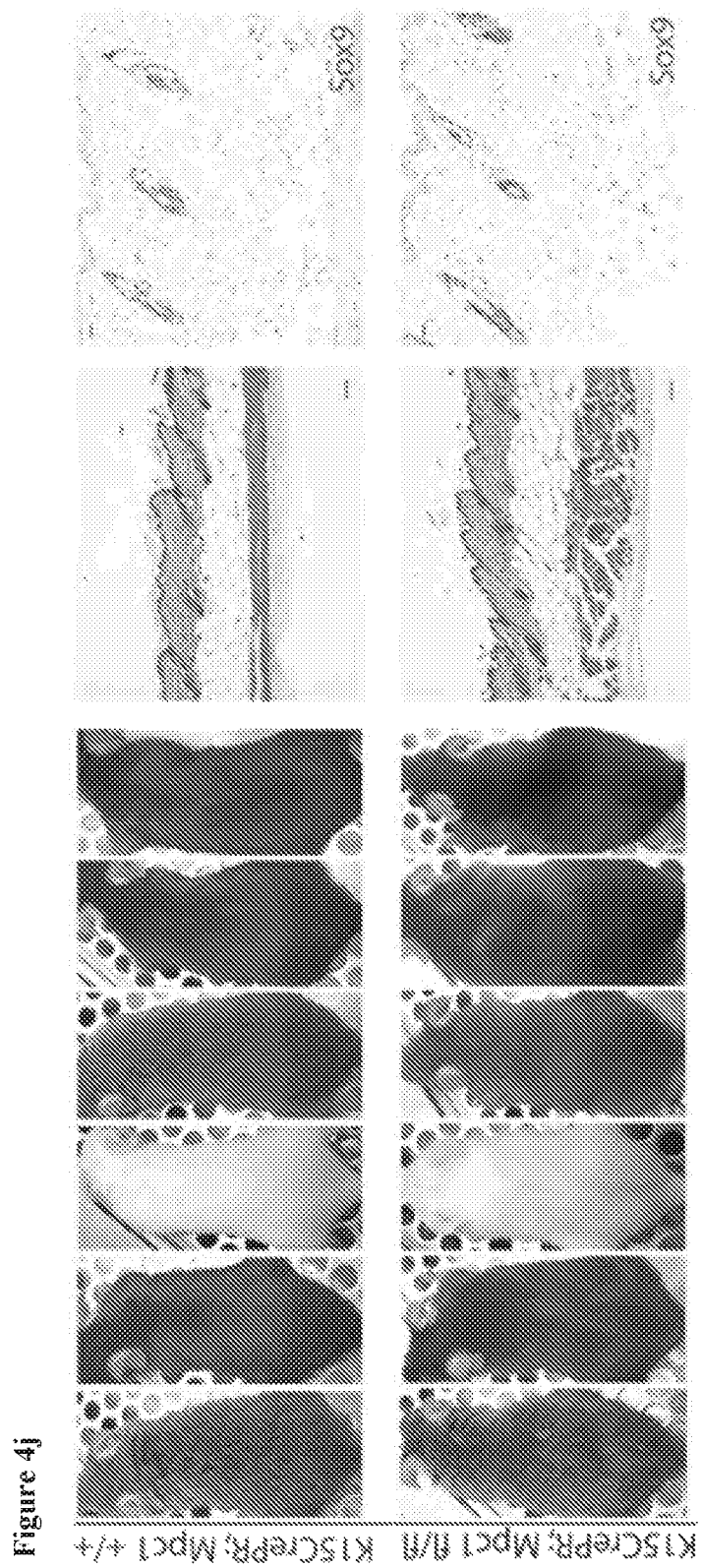
FIG. 4j, Six months after initiation of deletion of Mpc1 in HFSCs (K15CrePR;Mpc1fl/fl). mice lacking Mpc1 show no deleterious effects as measured by the hair cycle (left), pathology (middle, H and E), or staining for HFSCs (right, Sox9). Scale bars indicate 100 micrometers in middle panel, and 50 micrometers in right panel.
Figure 4K:
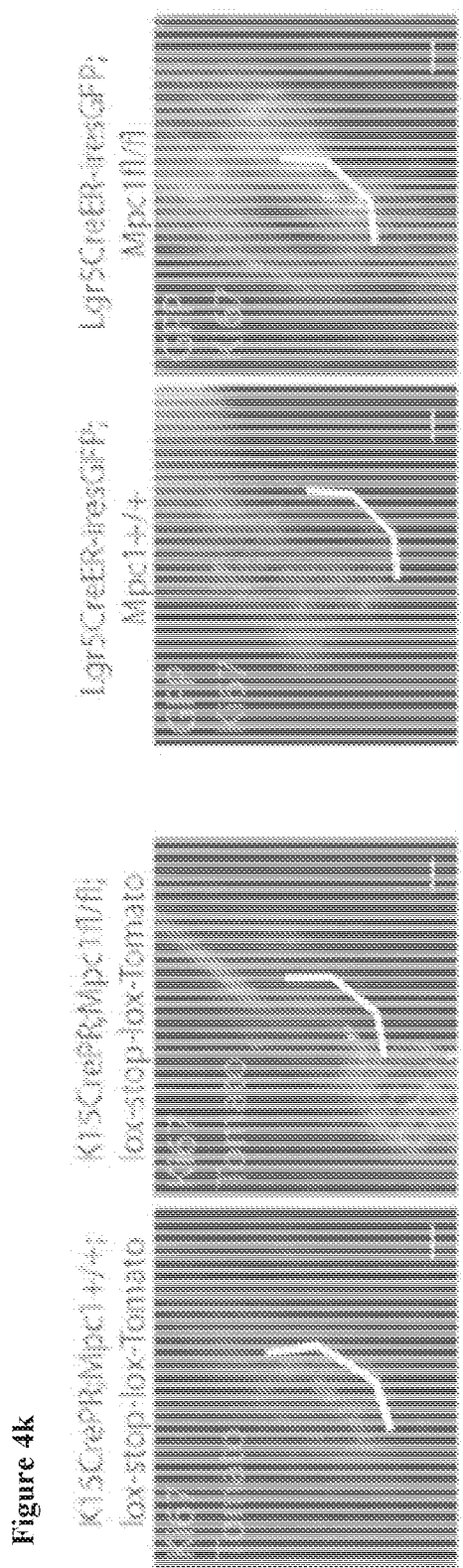
FIG. 4k, To demonstrate that the deletion of Mpc1 promotes proliferation specifically in HFSCs, we used K15CrePR;Ldha$^{fl/fl}$ mice bearing a lox-stop-lox-Tomato allele to look at K15+ HFSCs and proliferation with and without Mpc1 deletion (left). In addition, we took advantage of the ires-GFP within the Lgr5CreER allele to stain for Ki-67 and GFP and look for co-localization with and without Mpc1 deletion (right). White brackets denote bulge area. Scale bars represent 20 micrometers.
Figure 4I:
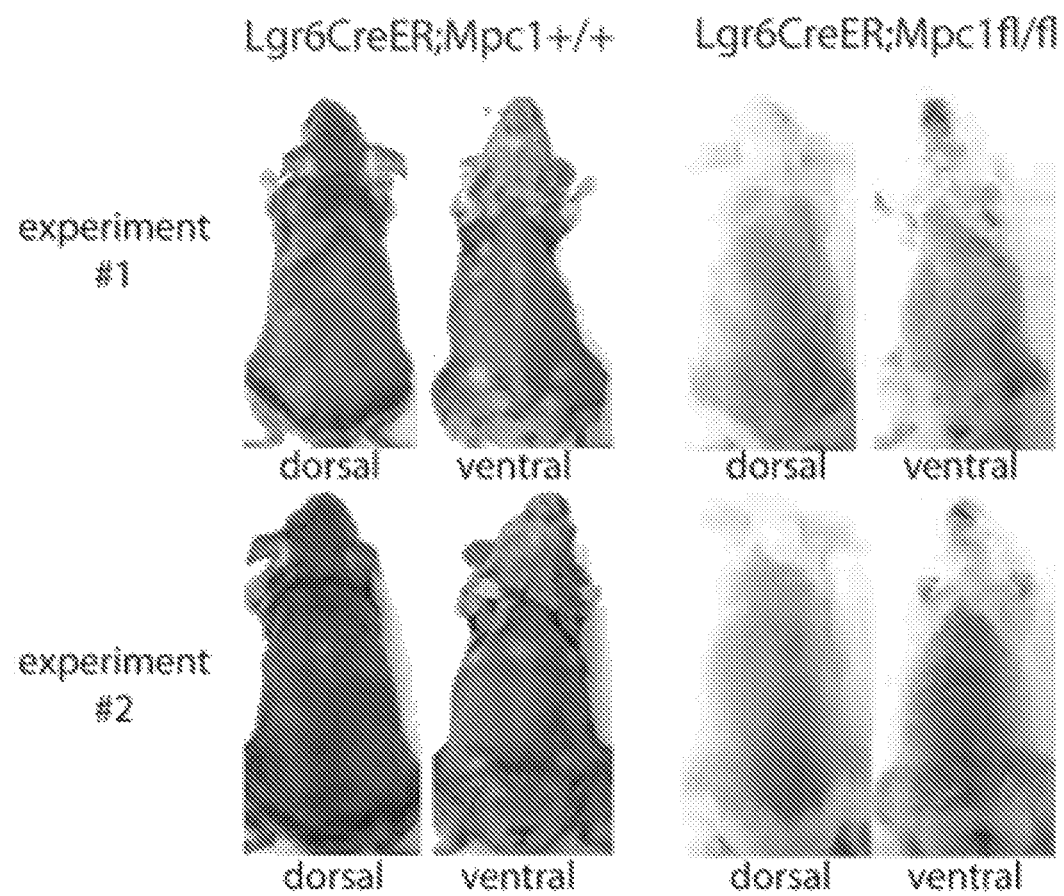
Figure 6A:
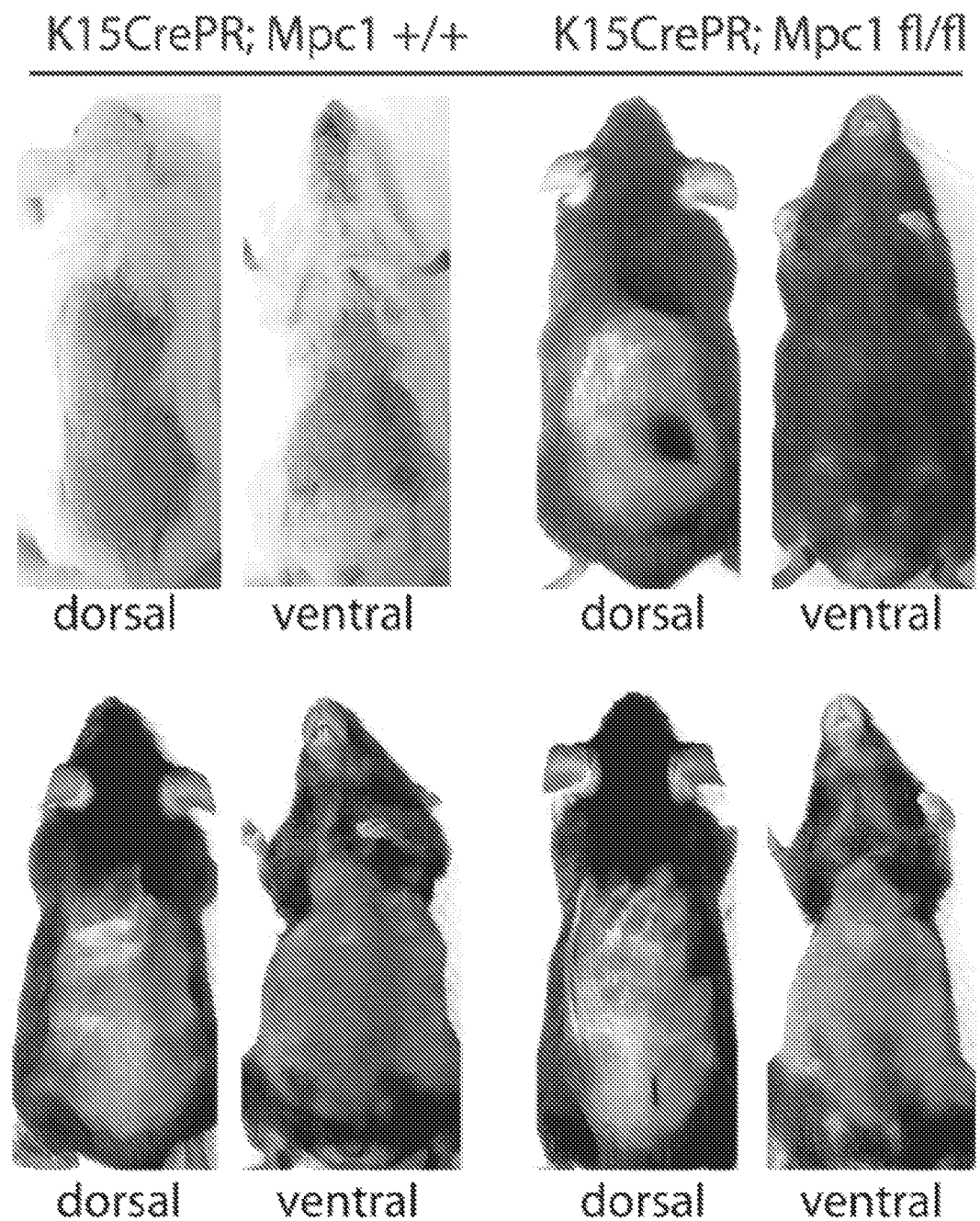
FIG. 6a, Additional replicate experiments for loss of MPC1 in HFSCs. Two independent experiments where loss of MPC1 in HFSCs was initiated by Mifepristone treatment at day 50.
Figure 6B:
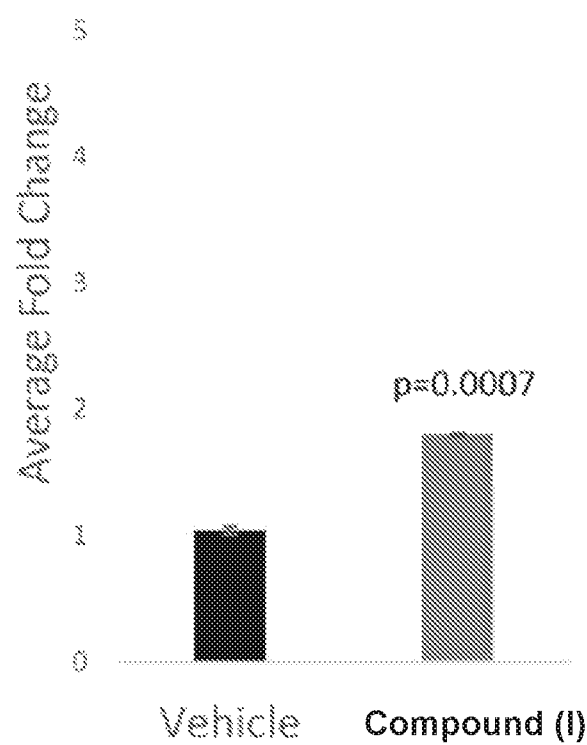
FIG. 6b, Additional replicate experiment of metabolomics analysis of lactate after 48-72 hours of treatment with the compound of formula (I). Experiments also showed an increase in lactate levels, similar to those shown in FIG. 3.

In animals with Mpc1 deletion in HFSCs, a strong acceleration of the ventral and dorsal hair cycles was observed with all the typical features of a telogen-anagen transition (FIG. 3a) (12 littermate pairs; additional animals presented in FIG. 6a). Mifepristone treated K15CrePR;Mpc1$^{fl/fl}$ animals were the only to show any signs of dorsal anagen by day 70. Western blotting on sorted HFSCs validated the loss of Mpc1 protein (FIG. 3b). Importantly, purified HFSCs lacking Mpc1 showed a strong induction of Ldh activity (FIG. 3c). Quantification of the dorsal hair cycle across three pairs of littermates showed a strong induction of anagen in backskin lacking Mpc1 (FIG. 3d), and histology showed that the anagen induction was normal in appearance with a typical hypodermal expansion (FIG. 3e). Immunostaining demonstrated the induction in Mpc1-null HFSCs of various markers of hair cycle activation such as Ki-67 and pS6, while Sox9 expression was unaffected (FIG. 3f). Long term deletion of Mpc1 did not lead to aberrant follicles or exhaustion of HFSCs as judged by pathology and staining for Sox9 (FIG. 4j). Furthermore, deletion of Mpc1 with Lgr5CreER showed a very similar phenotype as deletion with K15CrePR (FIG. 3f and FIG. 3g), validating the fact that deletion of this protein in HFSCs leads to their activation (n=12 pairs of littermates). Finally, immunofluorescence for the Ires-GFP of the Lgr5CreER transgene along with Ki-67 and lineage tracing with K15CrePR;Mpc1$^{fl/fl}$;lsl-Tomato mice also demonstrated that the HFSCs were indeed proliferative following induction of Mpc1 deletion by tamoxifen or mifepristone (FIG. 4k).

Figure 4M:
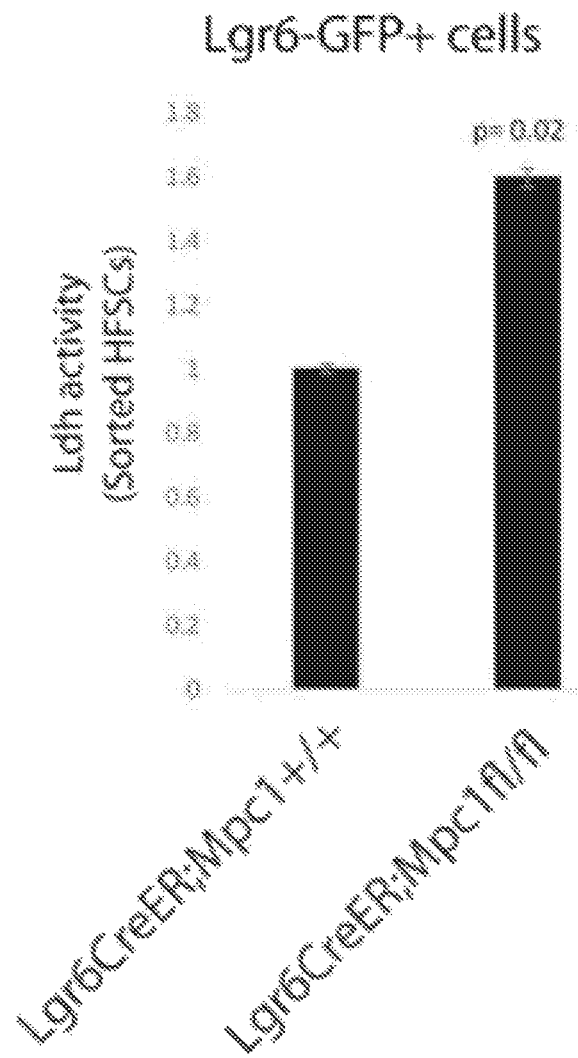
FIG. 4m, Ldh activity assay on sorted HFSCs from either control or Lgr6CreER mediated Mpc1 deletion mice showed increased activity in cells lacking Mpc1.
Figure 4N:
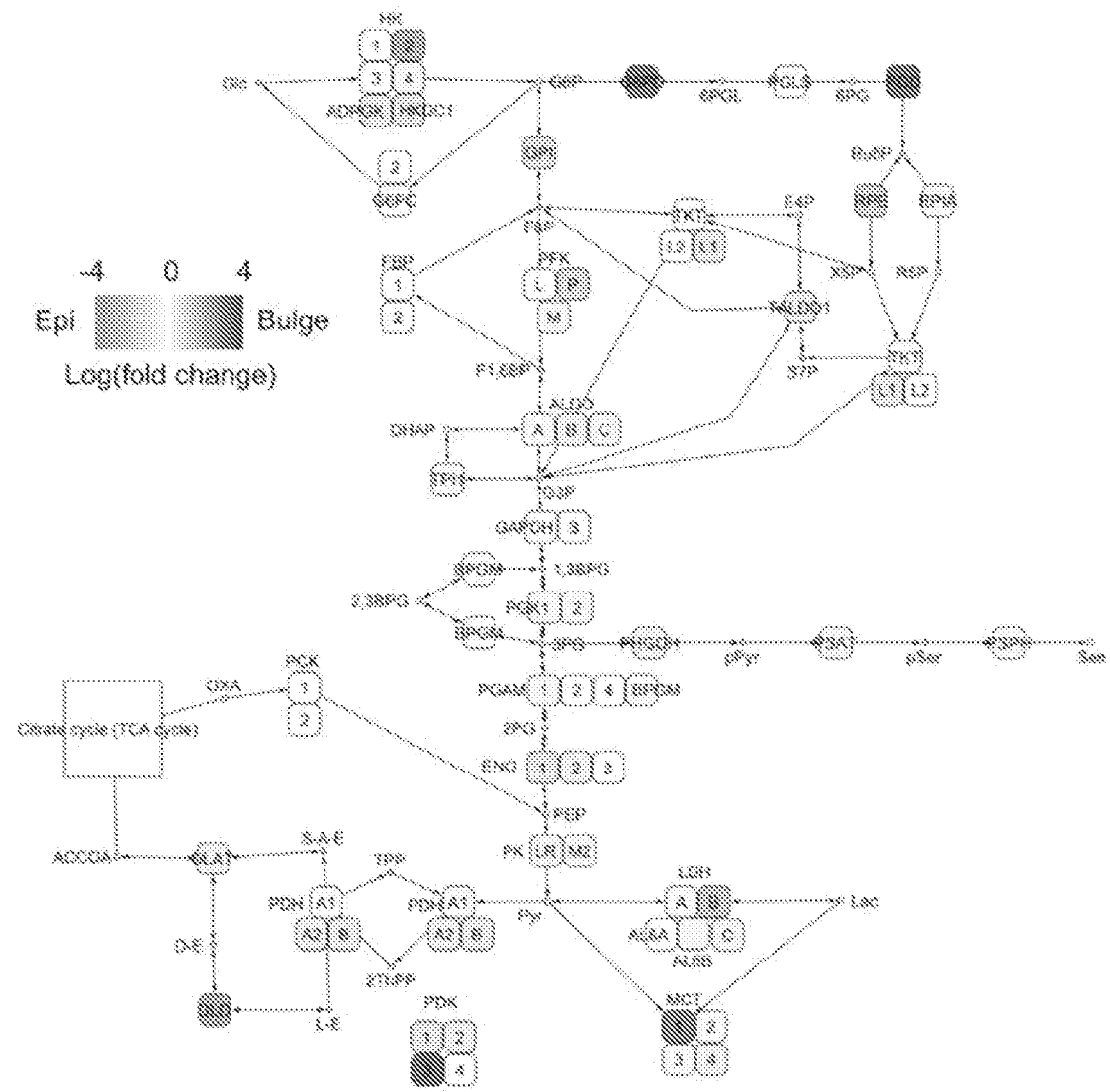
FIG. 4n, KEGG pathway analysis shows genes related to metabolic pathways induced in HFSCs (red) versus those suppressed (green).
Figure 5A:
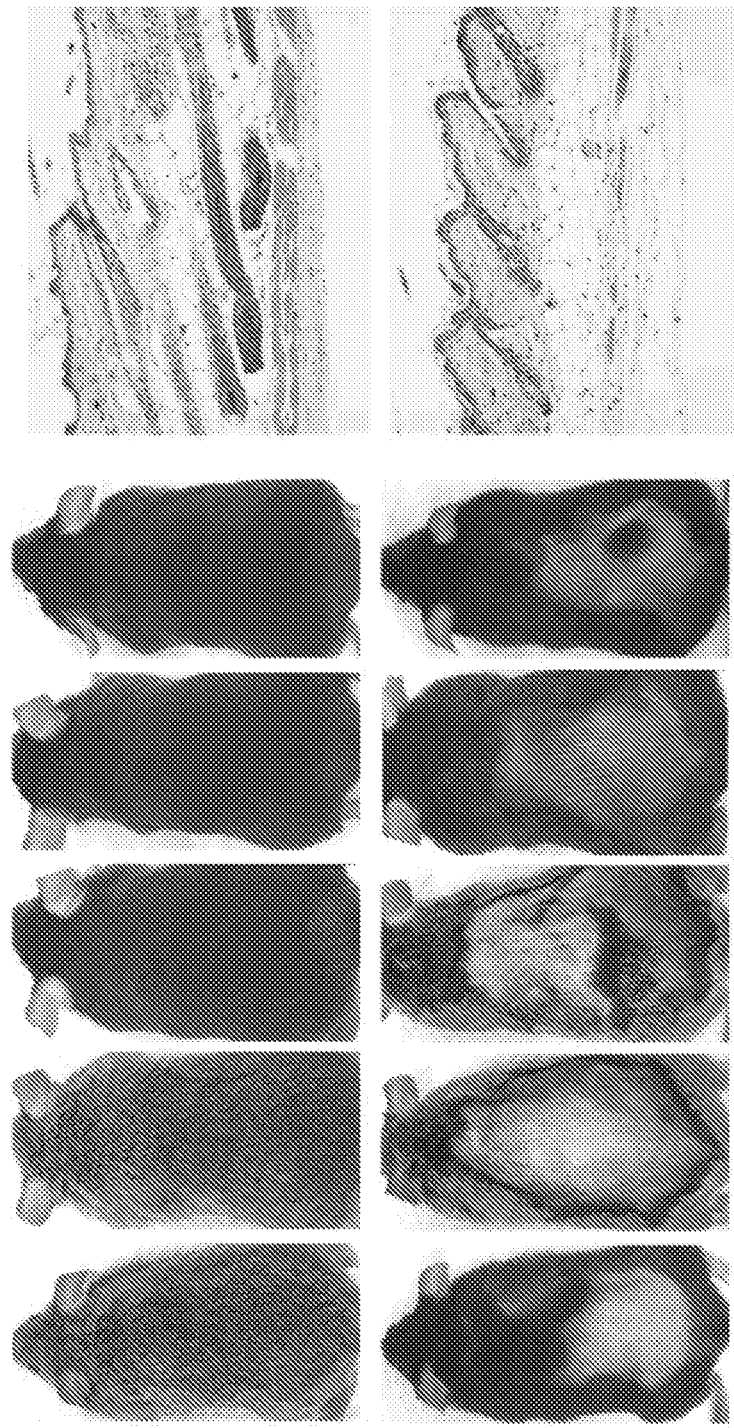
FIG. 5a, Ldha+/+ animals enter the hair cycle (anagen) synchronously at day 70 as measured by shaving and observation beginning at day 50. Ldha fl/fl animals which have Ldha deleted specifically in their HFSCs as controlled by Lgr5CreER, show profound defects in the entry into anagen. right. Skin pathology showing that Ldha+/+ animals enter a normal anagen typified by downgrowth of the follicle and hypodermal thickening, while Ldha fl/fl animals showed neither and remained in telogen.
Figure 5B:
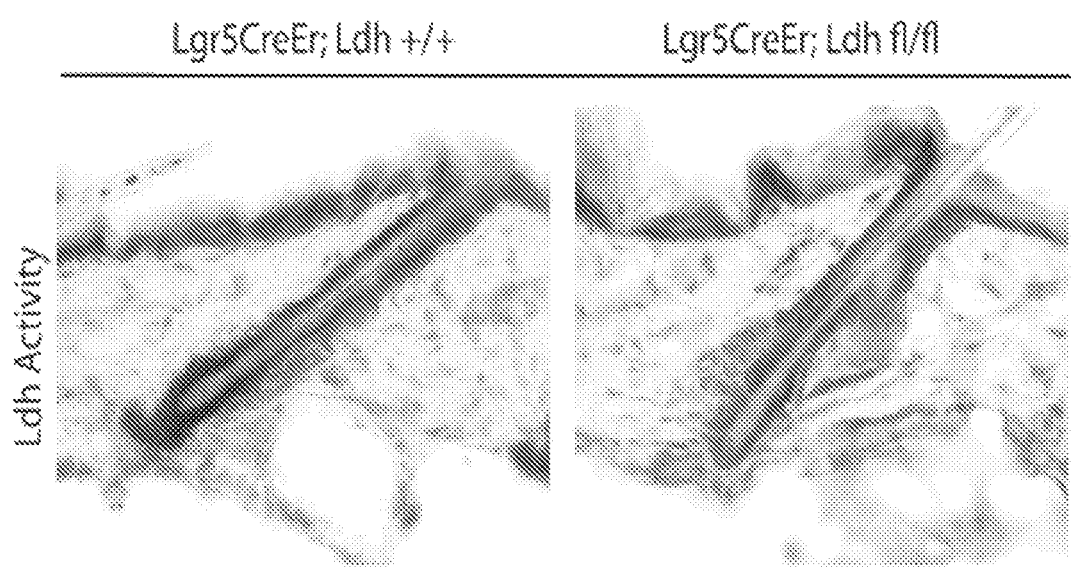
FIG. 5b, Ldh enzyme activity assay in the epidermis shows strong activity in HFSCs in Ldha+/+ animals, while Ldha fl/fl animals lacked this activity in the HFSCs, (HFSC niche indicated by bracket).

On the other hand, deletion of Mpc1 in the top of the follicle (infundibulum, sebaceous gland progenitors) and a limited number of interfollicular cells with Lgr6CreER[28] did not appear to affect the hair cycle (Lgr6CreER;Mpc1$^{fl/fl}$) (n=10 littermate pairs) or general skin homeostasis over at least 2 months (FIG. 4l). Ldh activity assay on Lgr6+ cells sorted from wildtype or deletion skin demonstrated that the Mpc1 deletion was effective (FIG. 4m). Together, these results indicate that increasing lactate production through the blockade of pyruvate into the TCA cycle has a strong effect on the ability of HFSCs, but not other cells in the hair follicle, to become activated to initiate a new hair cycle.

Figure 3I:
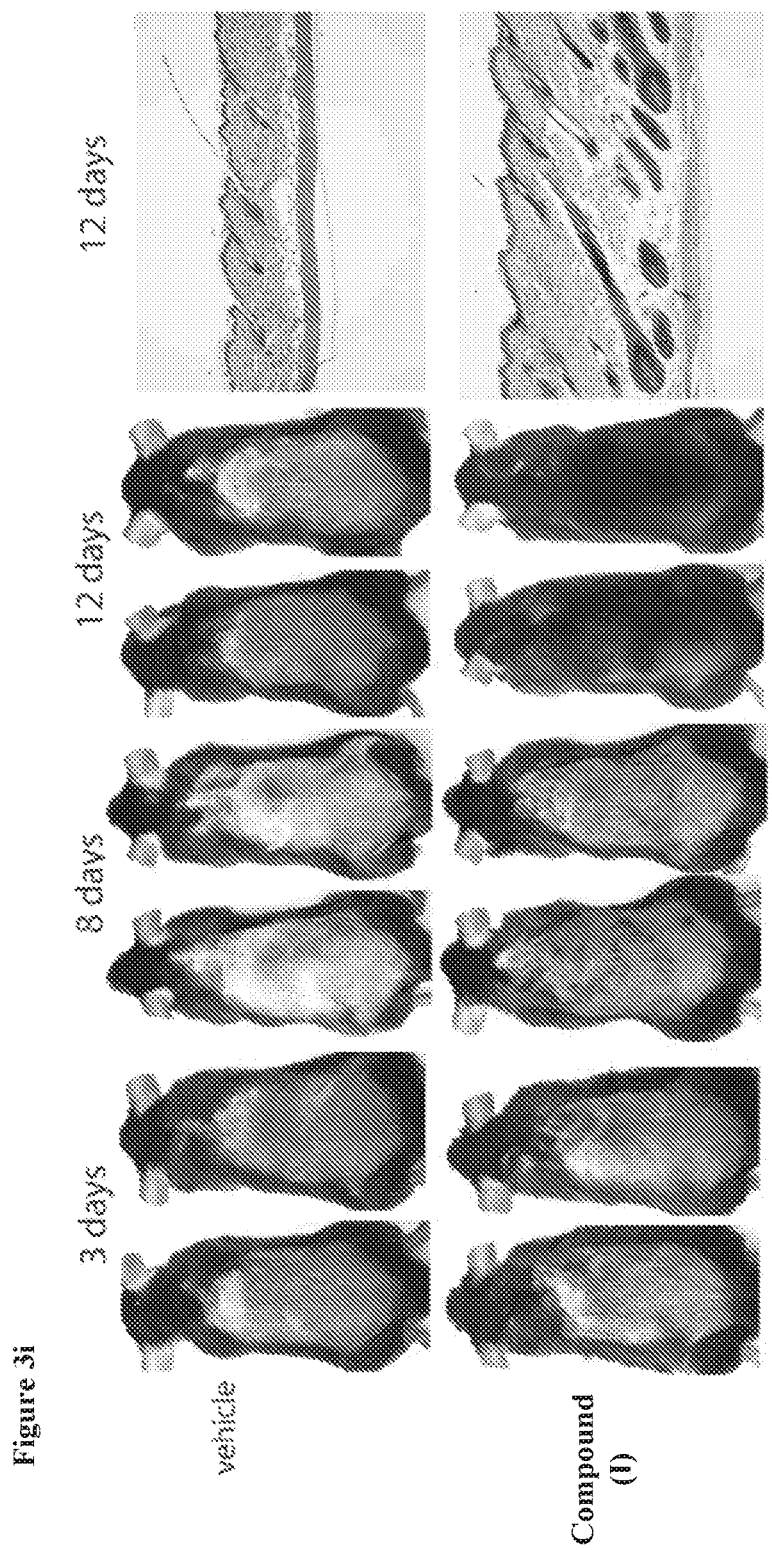
FIG. 3i, Animals treated topically with the compound of formula (I) (20 µM) showed pigmentation and hair growth, indicative of entry into anagen, after 8 days of treatment. Full anagen, indicated by full coat of hair, was achieved after 14 days of treatment. Mice treated topically with vehicle control did not show pigmentation nor hair growth even after 12 days of treatment. right, Skin pathology showing that animals treated with the compound of formula (I) entered an accelerated anagen at 8 weeks typified by down growth of the follicle and hypodermal thickening, while vehicle control treated animals showed neither and remained in telogen.
Figure 3J:
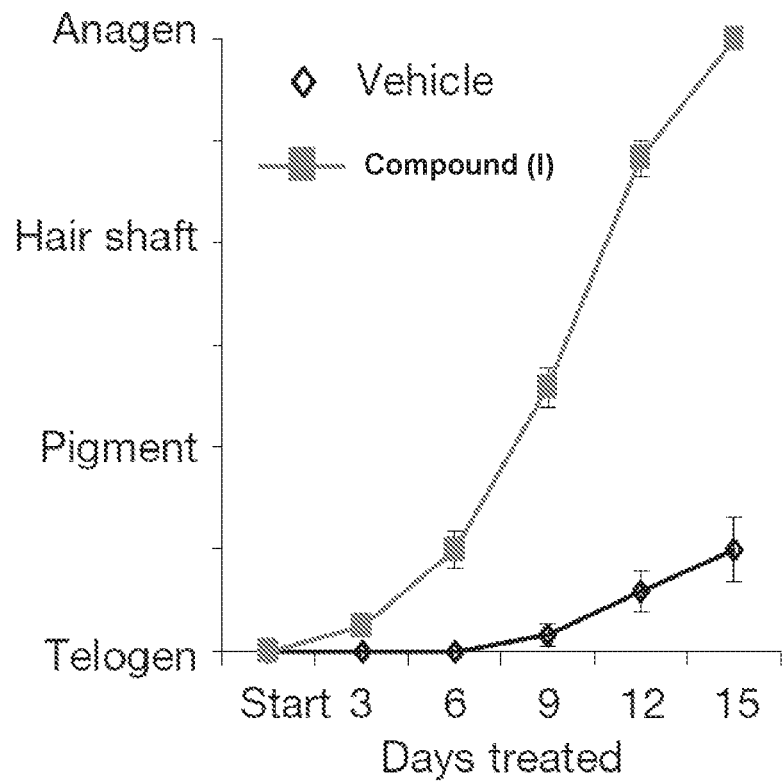
FIG. 3j, Graph showing time to observed phenotype in vehicle versus compound of formula (I) treated mice.
Figure 3K:
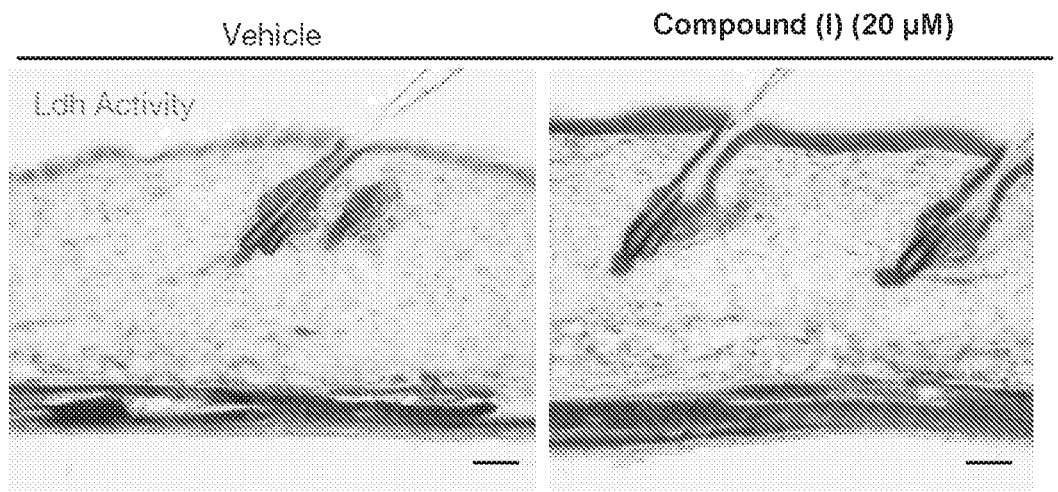
FIG. 3k, Ldh enzyme activity assay in the epidermis showed strong activity in HFSCs in vehicle control and compound of formula (I)-treated animals. Ldh enzyme activity was also seen in interfollicular epidermis of compound of formula (I)-treated animals. Ldh activity is indicated by dark stain; gray is nuclear fast red counterstain.
Figure 3I:
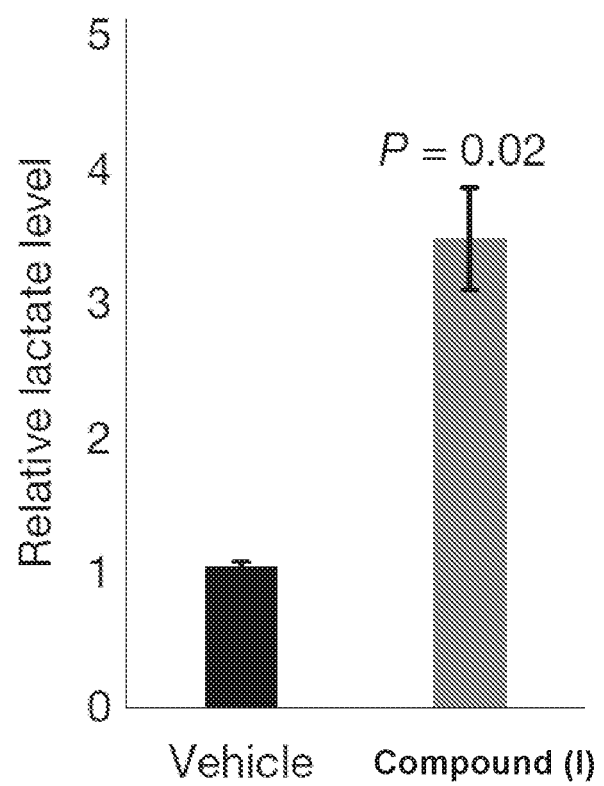

The compound of formula (I) is a well-established pharmacological inhibitor of the mitochondrial pyruvate carrier and known to promote lactate production as a result in various settings[17]. Topical treatment of animals in telogen (day 50) with the compound of formula (I) led to a robust acceleration of the hair cycle, as well as minor hyperproliferation of the interfollicular epidermis (FIG. 3i). Quantification of the hair cycle across at least 6 pairs of animals (vehicle vs the compound of formula (I)) indicated a strong acceleration of the hair cycle, beginning in as few as 3-5 days (FIG. 3j). Similar to genetic deletion of Mpc1, pharmacological blockade of the mitochondrial pyruvate carrier by topical application of the compound of formula (I) for 48 hours during telogen promoted increased Ldh activity in the interfollicular epidermis, consistent with increased capacity for lactate production (FIG. 3k). Finally, metabolomic analysis demonstrated that topical application of the compound of formula (I) increases total levels of lactate in sorted HFSCs (FIG. 3l).

Together, these data demonstrate that the production of lactate, through Ldha, is important for HFSC activation, and that HFSCs may maintain a high capacity for glycolytic metabolism at least in part through the activity of Myc. A genetic or pharmacological disruption of lactate production can modulate the activity of HFSCs.

Figure 7:
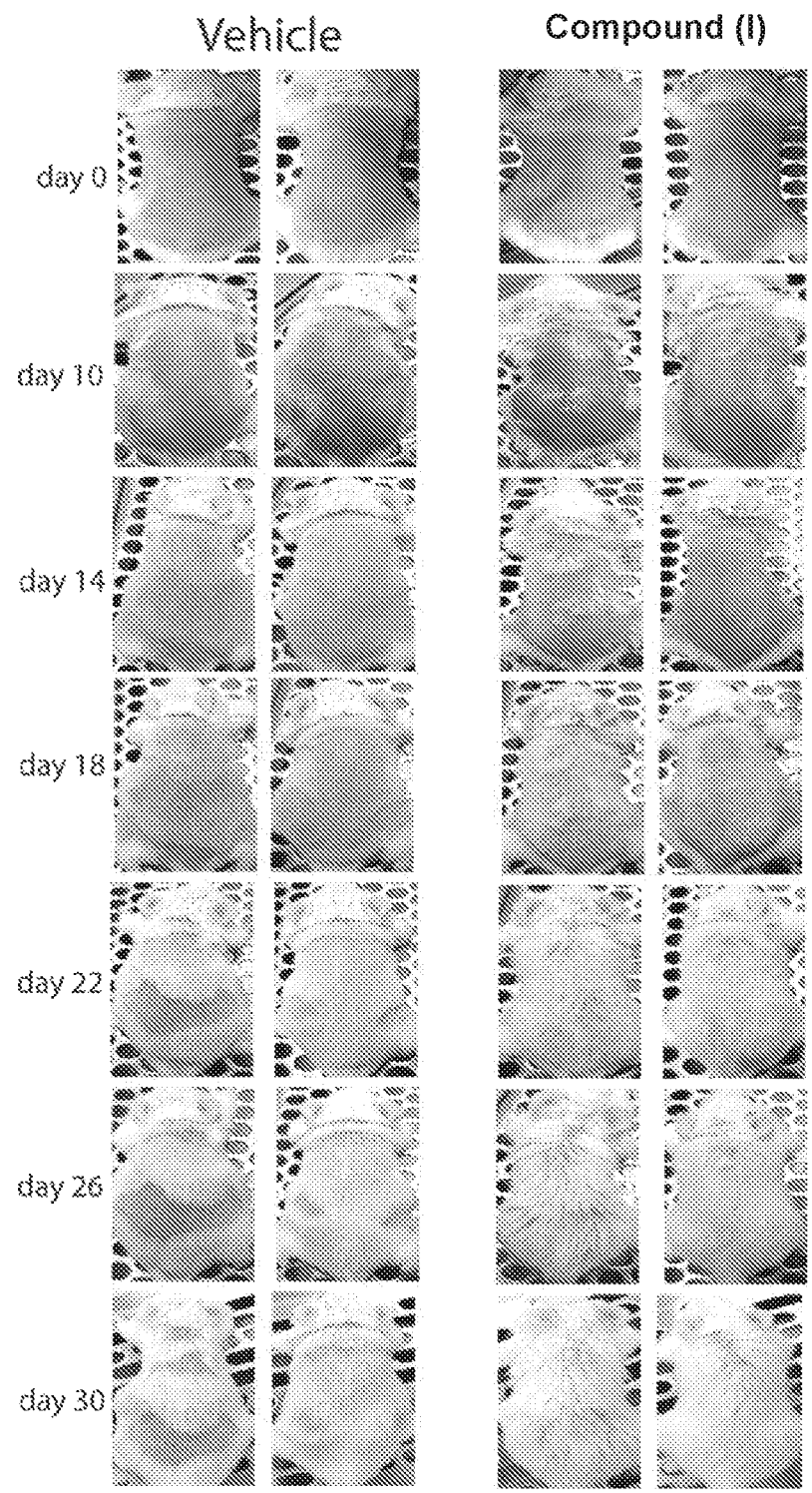
FIG. 7. Animals treated topically with the compound of formula (I) (20 µM) showed more complete hair growth. Mice treated topically with vehicle control showed patchy hair growth.

Example 4: Treatment of Elderly Mice Accelerated the Hair Cycle 17 month old mice were shaved and treated every other day with DMSO or 20 uM of the compound of formula (I) diluted in PLO gel (pluronic lecithin organogel). Images were acquired at the indicated day after shaving and carried out for 30 days. The aged mice treated with DMSO grew their coat back in a patchy pattern, while treatment with the compound of formula (I) led to a more complete re-growth (FIG. 7).

REFERENCES

1 Fuchs, E., Merrill, B. J., Jamora, C. & DasGupta, R. At the roots of a never-ending cycle. *Dev Cell* 1, 13-25 (2001).
2 Lavker, R. M. et al. Hair follicle stem cells: their location, role in hair cycle, and involvement in skin tumor formation. *The Journal of investigative dermatology* 101, 16S-26S (1993).
3 Blanpain, C., Lowry, W. E., Geoghegan, A., Polak, L. & Fuchs, E. Self-renewal, multipotency, and the existence of two cell populations within an epithelial stem cell niche. *Cell* 118, 635-648 (2004).
4 Tumbar, T. et al. Defining the epithelial stem cell niche in skin. *Science* 303, 359-363 (2004).
5 Morris, R. J. et al. Capturing and profiling adult hair follicle stem cells. *Nat Biotechnol* 22, 411-417 (2004).
6 Trempus, C. S. et al. Enrichment for living murine keratinocytes from the hair follicle bulge with the cell surface marker CD34. *J Invest Dermatol* 120, 501-511 (2003).
7 Nguyen, H., Rendl, M. & Fuchs, E. Tcf3 governs stem cell features and represses cell fate determination in skin. *Cell* 127, 171-183 (2006).
8 Lowry, W. E. et al. Defining the impact of beta-catenin/Tcf transactivation on epithelial stem cells. *Genes Dev* 19, 1596-1611 (2005).
9 Fromm, H. J. The nature of pyruvate involved in the enzymic formation of L-lactate in the rabbit-muscle lactate dehydrogenase reaction. *Biochim Biophys Acta* 99, 540-542 (1965).
Paus. R., Muller-Rover, S. & Botchkarev, V. A. Chronobiology of the hair follicle: hunting the "hair cycle clock". *J Investig Dermatol Symp Proc* 4, 338-345 (1999).
11 Wang, L., Siegenthaler, J. A., Dowell, R. D. & Yi, R. Foxc1 reinforces quiescence in self-renewing hair follicle stem cells. *Science* 351, 613-617, doi: 10.1126/science.aad5440 (2016).
12 Xie, H. et al. Targeting lactate dehydrogenase—a inhibits tumorigenesis and tumor progression in mouse models of lung cancer and impacts tumor-initiating cells. *Cell metabolism* 19, 795-809, doi: 10.1016/j.cmet.2014.03.003 (2014).
13 Kellenberger, A. J. & Tauchi. M. Mammalian target of rapamycin complex 1 (mTORC1) may modulate the timing of anagen entry in mouse hair follicles. *Exp Dermatol* 22, 77-80, doi: 10.1111/exd.12062 (2013).
14 Jaks, V. et al. Lgr5 marks cycling, yet long-lived, hair follicle stem cells. *Nat Genet* 40, 1291-1299, doi: 10.1038/ng.239 (2008).
15 Bricker, D. K. et al. A mitochondrial pyruvate carrier required for pyruvate uptake in yeast, Drosophila, and humans. *Science* 337, 96-100, doi:10.1126/science.1218099 (2012).
16 Schell, J. C. et al. A role for the mitochondrial pyruvate carrier as a repressor of the Warburg effect and colon cancer cell growth. *Mol Cell* 56, 400-413, doi: 10.1016/j.molcel.2014.09.026 (2014).
17 Patterson, J. N. et al. Mitochondrial metabolism of pyruvate is essential for regulating glucose-stimulated insulin secretion. *J Biol Chem* 289, 13335-13346, doi: 10.1074/jbc.M113.521666 (2014).
18 Hsu, P. & Qu, C. K. Metabolic plasticity and hematopoietic stem cell biology. *Current opinion in hematology* 20, 289-294, doi:10.1097/MOH.0b013e328360ab4d (2013).

19 Harris, J. M. et al. Glucose metabolism impacts the spatiotemporal onset and magnitude of HSC induction in vivo. *Blood* 121, 2483-2493, doi: 10.1182/blood-2012-12-471201 (2013).
Takubo, K. et al. Regulation of glycolysis by Pdk functions as a metabolic checkpoint for cell cycle quiescence in hematopoietic stem cells. *Cell Stem Cell* 12, 49-61, doi: 10.1016/j.stem.2012.10.011 (2013).
21 Simsek, T. et al. The distinct metabolic profile of hematopoietic stem cells reflects their location in a hypoxic niche. *Cell Stem Cell* 7, 380-390, doi:10.1016/j.stem.2010.07.011 (2010).
22 Shin, J. et al. Single-Cell RNA-Seq with Waterfall Reveals Molecular Cascades underlying Adult Neurogenesis. *Cell Stem Cell* 17, 360-372, doi: 10.1016/j.stem.2015.07.013 (2015).
23 Ito, M. et al. Stem cells in the hair follicle bulge contribute to wound repair but not to homeostasis of the epidermis. *Nat Med* 11, 1351-1354 (2005).
24 Subramanian. A. et al. Gene set enrichment analysis: a knowledge-based approach for interpreting genome-wide expression profiles. *Proc Natl Acad Sci USA* 102, 15545-15550, doi:10.1073/pnas.0506580102 (2005).

INCORPORATION BY REFERENCE

All US and PCT patent application publications and US patents cited herein are hereby incorporated by reference in their entirety as if each individual publication or patent was specifically and individually indicated to be incorporated by reference. In case of conflict, the present application, including any definitions herein, will control.

The invention claimed is:

1. A method of accelerating, promoting, or restoring hair growth, comprising administering to a subject in need thereof an effective amount of a compound of formula (I):

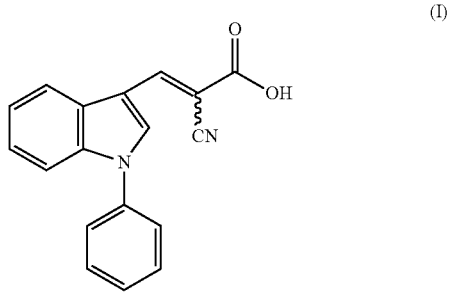 [SMILES: N#CC(=Cc1cn(-c2ccccc2)c2ccccc12)C(=O)O]

or a pharmaceutically acceptable salt thereof.

2. The method of claim 1, wherein administering comprises topically applying a composition comprising the compound to an affected area.

3. The method of claim 1, wherein the subject exhibits symptoms selected from alopecia, hair loss, hair thinning, and baldness.

4. The method of claim 1, wherein the subject exhibits symptoms selected from hair loss, hair thinning, and baldness.

5. The method of claim 1, wherein the subject exhibits baldness.

6. The method of claim 5, wherein the baldness is male pattern baldness or female pattern baldness.

7. The method of claim 1, wherein the subject exhibits symptoms selected from hair loss and hair thinning.

8. The method of claim 7, wherein the hair loss or the hair thinning is caused by anagen effluvium or telogen effluvium.

9. The method of claim 3, wherein the alopecia is selected from juvenile alopecia, premature alopecia, senile alopecia, alopecia areata, androgenic alopecia, mechanical alopecia, and symptomatic alopecia.

10. The method of claim 1, wherein the compound is applied to a hair follicle.

11. The method of claim 1, wherein the compound of formula (I) is administered daily.

12. The method of claim 1, wherein the subject is a mammal.

13. The method of claim 1, wherein the subject is a human.

14. The method of claim 1, wherein: administering comprises topically applying a composition comprising the compound to an affected area; the subject exhibits symptoms selected from alopecia, hair loss, hair thinning, and baldness; and the subject is human.

15. The method of claim 14, wherein the subject exhibits symptoms of baldness.

16. The method of claim 15, wherein the baldness is male pattern baldness or female pattern baldness.

17. The method of claim 14, wherein the subject exhibits symptoms of alopecia.

18. The method of claim 17, wherein the alopecia is selected from juvenile alopecia, premature alopecia, senile alopecia, alopecia areata, androgenic alopecia, mechanical alopecia, and symptomatic alopecia.

19. The method of claim 14, wherein the subject exhibits symptoms selected from hair loss and hair thinning.

20. The method of claim 19, wherein the hair loss or the hair thinning is caused by anagen effluvium or telogen effluvium.

* * * * *